US012376891B2

(12) United States Patent
Grob et al.

(10) Patent No.: US 12,376,891 B2
(45) Date of Patent: Aug. 5, 2025

(54) SURGICAL METHODS FOR THE TREATMENT OF SPINAL STENOSIS

(71) Applicant: Woodwelding AG, Stansstad (CH)

(72) Inventors: Dieter Grob, Erlenbach (CH); Jörg Mayer, Niederlenz (CH); Johan Van Havermaet, Deinze (BE); Randal R. Betz, Bradenton, FL (US)

(73) Assignee: WOODWELDING AG, Stansstad (CH)

( * ) Notice: Subject to any disclaimer, the term of this patent is extended or adjusted under 35 U.S.C. 154(b) by 666 days.

(21) Appl. No.: 17/299,123

(22) PCT Filed: Dec. 4, 2019

(86) PCT No.: PCT/EP2019/083732
§ 371 (c)(1),
(2) Date: Jun. 2, 2021

(87) PCT Pub. No.: WO2020/115163
PCT Pub. Date: Jun. 11, 2020

(65) Prior Publication Data
US 2022/0071663 A1 Mar. 10, 2022

Related U.S. Application Data

(63) Continuation of application No. 16/209,029, filed on Dec. 4, 2018, now Pat. No. 11,224,465.

(51) Int. Cl.
*A61B 17/70* (2006.01)
*A61B 17/00* (2006.01)
(Continued)

(52) U.S. Cl.
CPC ........ *A61B 17/707* (2013.01); *A61B 17/0401* (2013.01); *A61B 17/1671* (2013.01);
(Continued)

(58) Field of Classification Search
CPC ............ A61B 17/7071; A61B 17/7067; A61B 17/7062; A61B 17/707; A61B 2017/0414; A61B 2017/045
See application file for complete search history.

(56) References Cited

U.S. PATENT DOCUMENTS

| 6,737,149 | B1 | 5/2004 | Wintermantel et al. |
| 7,335,205 | B2 * | 2/2008 | Aeschlimann .......... B29C 66/21 606/232 |

(Continued)

FOREIGN PATENT DOCUMENTS

| WO | 2012/100358 | 8/2012 |
| WO | 2012/100359 | 8/2012 |

*Primary Examiner* — Eduardo C Robert
*Assistant Examiner* — Holly Joanna Lane
(74) *Attorney, Agent, or Firm* — Rankin, Hill & Clark LLP

(57) ABSTRACT

A method and suture anchor for treatment of spinal stenosis. The method includes the steps of cutting off a muscle origin or insertion from a spinous process, cutting off the spinous process at the transition to the lamina arcus vertebrae, at least partial resection of the lamina arcus vertebrae and thereby decompression of the spinal cord within the foramen vertebral, performing osteosynthesis of the spinous process, and placing a suture anchor within the spinous process and reattaching the muscle origin or insertion to the spinous process. Further methods for spine stabilization are provided wherein suture anchors are used to implement a tension band wiring. Further methods for reduction of unwanted effects after spinal treatment are provided.

13 Claims, 9 Drawing Sheets

(51) Int. Cl.
*A61B 17/04* (2006.01)
*A61B 17/16* (2006.01)
A61B 17/02 (2006.01)
A61B 17/86 (2006.01)

(52) U.S. Cl.
CPC ............... *A61B 17/7067* (2013.01); *A61B 2017/00469* (2013.01); *A61B 2017/0256* (2013.01); *A61B 17/1659* (2013.01); *A61B 17/86* (2013.01)

(56) References Cited

U.S. PATENT DOCUMENTS

| | | | |
|---|---|---|---|
| 2003/0023268 A1* | 1/2003 | Lizardi | A61B 17/0401 606/232 |
| 2006/0293675 A1* | 12/2006 | Li | A61B 17/0401 606/232 |
| 2011/0084959 A1* | 4/2011 | Kim | G06F 1/3265 345/76 |
| 2012/0078300 A1* | 3/2012 | Mayer | A61B 17/0401 606/232 |
| 2012/0197316 A1* | 8/2012 | Mayer | A61B 17/0401 606/328 |
| 2013/0261677 A1* | 10/2013 | Bouduban | A61B 17/0401 606/323 |
| 2017/0222432 A1* | 8/2017 | Iwasawa | B60R 16/02 |

* cited by examiner

SURGICAL METHODS FOR THE TREATMENT OF SPINAL STENOSIS

CROSS-REFERENCE TO RELATED APPLICATION

The present application is a national stage of PCT/EP2019/08732 filed Dec. 4, 2019, which claims priority to U.S. Ser. No. 16/209,029 filed Dec. 4, 2018.

BACKGROUND OF THE INVENTION

Field of the Invention

The invention is in the field of surgical procedures and concerns in particular to methods for spinal surgery. The inventive methods refer mainly to the treatment of spinal stenosis, which may be caused by spinal osteoarthritis or degenerative disc disease.

Description of Related Art

Spinal stenosis is the narrowing of the spinal column in one or more areas, which may lead to the compression of the spinal cord and spinal nerves. Spinal decompression surgery is a general term that refers to various procedures intended to relieve symptoms caused by pressure, or compression, on the spinal cord and/or nerve roots. Bulging or collapsed disks, thickened joints, loosened ligaments, and bony growths can narrow the spinal canal and the spinal nerve openings (foramen), causing irritation. Spinal stenosis can occur in the cervical, lumbar or thoracic region of the spine, and often results in chronic back and neck pain. This disorder usually involves the narrowing of one or more of the following: (1) the canal in the center of the vertebral column through which the spinal cord and nerve roots run, (2) the canals at the base or roots of nerves branching out from the spinal cord, or (3) the openings between vertebrae through which nerves leave the spine and go to other parts of the body.

Spinal stenosis treatment options range from conservative to the more aggressive and depends on the severity of the symptoms. In the event that the symptoms have reached a level where the condition is debilitating and non-surgical treatments have failed to alleviate pain, surgery for spinal stenosis treatment may be required for long-term relief. Since spinal stenosis is at its core a condition that compresses the spinal canal, any surgery for spinal stenosis would have to relieve that compression in order to alleviate the symptoms associated with it. The primary goal of any decompression surgery of the spine is to provide additional space for the constricted spinal cord, nerve roots or nerves to pass through. Once this space has been opened up, the pain, inflammation, and numbness associated with spinal stenosis should subside. A decompression surgery for spinal stenosis is performed in order to return any lost mobility or motor skills associated with the condition as well.

Laminectomy or laminotomy are surgical methods to treat spinal stenosis. These procedures involve removing a small part of the bony arches of the spinal canal, called the lamina. During a laminotomy, just a section of the lamina is removed. During a laminectomy, the entire lamina is removed. Removing the lamina enlarges the spinal canal, thus relieving the pressure on compressed nerves. Lumbar fusion is frequently preformed in conjunction with laminectomy. Current fusion techniques increase the risk of spinal stenosis procedures. Various fusion techniques require the severing and/or removal of certain structural soft tissues (e.g. muscle attachments, ligaments) surrounding the spine.

Alternative methods are a foraminotomy or foraminectomy. Both procedures are performed to expand the openings for the nerve roots to exit the spinal cord by removing some bone and other tissue. A foraminectomy generally refers to a procedure that removes a large amount of bone and tissue. The above described techniques may be combined with osteophyte removal, involving removing bony growths called osteophytes or bone spurs. Further corpectomy may be necessary. This is a method removing the body of a vertebra, as well as the disks.

A combination of techniques may be used; and in some cases, fusion of the vertebrae also is needed to stabilize the spine. Increasingly, surgeons are looking for improved methods of effecting less invasive treatments for spinal stenosis. The device must be able to be safely and consistently implanted without excess damage to the patient. The present invention is directed at overcoming, or at least improving upon, the disadvantages of the prior art.

SUMMARY OF THE INVENTION

It is accordingly an object of the present invention to provide method with which the above disadvantages could at least partially be overcome or alleviated and/or to provide a more useful alternative to the known methods of spinal decompression. In particular, it is an object to provide a novel method for laminectomy or laminotomy with less harm to autochthone back muscles. The newly developed methods in spine surgery are based on the use of suture anchors which allow to anchor a suture within a very short bone opening, so that the anchors may be located in structures allowing only little room for anchoring.

The methods of the present invention are especially suitable for the treatment of a spinal stenosis. A first aspect of the present invention refers to a method for the treatment of spinal stenosis including the following steps:

cutting off a muscle origin or insertion from a spinous process cutting off the spinous process at the transition to the lamina arcus vertebrae at least partial resection of the lamina arcus vertebrae and thereby decompression of the spinal cord within the foramen vertebral performing osteosynthesis of the spinous process and placing a suture anchor within the spinous process and reattaching the muscle origin or insertion to the spinous process.

The method according to the first aspect of the invention is suitable to treat nearly all vertebrae. Thus, the first aspect of the invention includes methods, wherein the spinal stenosis is a cervical spinal canal stenosis, thoracic spinal canal stenosis, lumbar spinal canal stenosis or wide spinal canal stenosis.

As any common surgical method, the methods of the invention may further include the step of surgical incision (cut made through the skin to facilitate the following surgical method or procedure) or multiple incisions. The location and size of the incision depends on the vertebrae to be treated. One possibility is that the back is approached through a 5 to 10 centimeter long incision in the midline of the back. The step of incision is commonly followed by preparing access from the outside of a body to a spine region of interest or respectively the spinous process of a vertebral body of interest.

Commonly, the left and right back muscles (erector spinae) are dissected off the vertebra on both sides and at multiple levels. Performing the method of the first aspect of the invention has the advantageous that the spinous process has only to be detached from the muscles of one body side. This reduces the injury done to the surrounding muscles, which allows for reattachment of the cut off muscles to the spinous process and intact muscle insertion respectively origin, increases the stability of the spine after the surgery and speeds up the recovery of the patients. Therefore, one embodiment of the first aspect refers to methods, wherein the one or more muscle origins, respectively muscle insertions are cut off only on the left side or on the right side but not on both sides of the spinous process (respectively the body). Thereby at least one muscle attachment (insertion or origin) of at least one muscle has to be cut off from the spinous process. The origin or insertion of the at least one muscle to be cut off may be selected from the group consisting of multifidus muscles and rotatores muscles (brevi and longi), the muscle splenius capitis, splenius cervicis, semispinalis cervicis (or semispinalis colli), semispinalis thoracis (or semispinalis dorsi), and spinal erectors (Mm. longissimus thoracis, spinalis thoracis, spinalis cervicis, and spinalis capitis).

The erector spinae are not just one muscle, but a group of muscles and tendons which run more or less the length of the spine on the left and the right, from the sacrum or sacral region and hips to the base of the skull. These muscles lie either side of the vertebral column spinous processes and extend throughout the lumbar, thoracic, and cervical regions (lower, middle, and upper back and the neck). The erector spinae is covered in the lumbar and thoracic regions (lower back and lower middle back) by the thoracolumbar fascia, and in the cervical region (neck) by the nuchal ligament. The longissimus muscle is the intermediate and the largest of the three columns. It has three parts with different origin and insertion. Only the longissimus thoracis originates in parts from spinous processes (of the lumbar vertebrae). The spinalis muscle is the smallest and most medial column. It has also three parts wherein the spinalis thoracis originates from the spinous process of L3-T10 and inserts in the spinous process of T8-T2 and the spinalis cervicis originates from the spinous process of T2-C6 and inserts in the spinous process of C4-C2.

Most skeletal muscles are attached to bone on its ends by way of what we call tendons. Nevertheless, the structure that muscles are attached to may be a bone, a tendon or the subcutaneous dermal connective tissue (enthesis). Thereby, enthesis is the connective tissue between tendon or ligament and the bone. As the muscles contract, they exert force on the bones, which help to support and move our body along with its appendages. The insertion and origin of a muscle are the two places where it is anchored, one at each end. In most cases, one end of the muscle is fixed in its position, while the other end moves during contraction. The origin is the attachment site that doesn't move during contraction, while the insertion is the attachment site that does move when the muscle contracts. Alternatively worded, the origin of a muscle is at the bone, typically proximal, which has greater mass and is more stable during a contraction than a muscle's insertion. Depending on the vertebrae to be treated different muscles are attached to the spinous process. The spinous process may include muscle origin as well as muscle insertion. This also varies between different vertebrae. The method of the present invention includes a step including cut off at least one muscle origin or insertion from a spinous process. This means that the surgeon has to cut through at least one structure attaching a muscle to the spinous process. However, in case that more than one muscle is attached to the respective spinous process, it may be necessary to cut more than one muscle attachment. In general it is possible to cut all muscles attached to the spinous process but it is preferred to cut off only muscles of one body side. Thus, one embodiment of the first aspect of the invention relates to a method, wherein the origin or insertion of all muscles originating or inserting on one side of the spinous process are cut off. Therefore, the methods of the present invention allows bilateral decompression via unilateral approach.

In general, least possible muscles may be cut off. It should be ensured that the following steps of the procedure can be carried out without hindering of muscles. One of these steps is: cutting off the spinous process (osteotomy) at the transition to the lamina arcus vertebrae. This cut is along or at least approximately along a coronal plane. An alternative wording for that step is therefore: separation of the spinous process from the lamina arcus vertebrae. Subsequently the spinous process and also the muscles still attached to it may be pushed away. The spinous process being cut off the vertebrae may be moved towards the side where no muscle is cut off (or respectively to the body side where all muscles are still attached to the spinous process). Muscles covering the lamina may be carefully pushed away to expose the bony structure. Consequently, one embodiment of the first aspect may be a method for the treatment of spinal stenosis including the following steps: incision and preparing access from the outside of a body to a spine region of interest, cutting off at least one muscle origin or insertion from a spinous process, cutting off the spinous process (osteotomy) at the transition to the lamina arcus vertebrae and pushing the spinous process together with the muscles not cut aside, partial resection of the lamina arcus vertebrae and thereby decompression of the spinal cord within the foramen vertebral, osteosynthesis of the spinous process, placing a suture anchor within the spinous process and reattaching the at least one muscle origin or insertion to the spinous process.

After cutting off the spinous process and pushing away the spinous process as well as the muscles attached to it there should be enough space to reach the lamina arcus vertebrae and introduce a tool for cutting bone (e.g. an ultrasound driven blade). Therefore, the next step is at least a partial resection of the lamina arcus vertebrae and thereby decompression of the spinal cord within the foramen vertebral. It may be that the partial resection of the lamina arcus vertebrae is sufficient for an adequate decompression. Nevertheless, it may also be that the lamina has to be removed completely. In addition, the surgeon may have to introduce a further tool (or may even use the same as for partial resection) for ablating bone (e.g., degenerative alterations, such as osteophytes) within the foramen vertebral or for removal of spondylophytes narrowing the foramen intervertebral. In general the method according to the first aspect may optionally includes the following step: removing additional (bone) structures causing a stenosis and a compression of the spinal cord or a spinal nerve. Thereby the structures to be removed may be selected from the group consisting of: bony overgrowth such as osteophytes or spondylophytes (degenerative bony structures at the facet joints and pedicles), hypertrophic ligamentum flavum, hernia of the disc, synovial cysts and spinal tumors.

After decompression the spinous process has to be reattached to the lamina. Therefore, the inventive methods includes a step of osteosynthesis of the spinous process. This is done using a plate which is adapted to the vertebra to be treated. It fits to the curvature forming the transition between lamina and spinous process. The plate should lie over the cut through the basis of the spinous process. Advantageously, the plate is fixed on each side next to the cut using anchors including a material having thermoplastic properties and are anchored in the bone opening with the aid of vibratory energy used for in situ liquefaction of the material having thermoplastic properties. It is advantageously, that the plate is attached to the bone using a pin or anchor that can be fixed unicortical. This means that the distal layer of dense bone which encloses the spinal cord is not pierced. In addition, the length of the pin may be adapted to the length of the bone opening during the in situ liquefaction of the material having thermoplastic properties. Therefore, the tip of the pin has to be made of the material having thermoplastic properties so that it melt and that the liquefied material flows into the surrounding spongy parts of the bone. Thus, the bone structure is not weakened like it is when using a screw or barbed anchor.

Thereafter the muscles has to be reattached to the spinous process. Therefore at least one suture anchor is implanted within the spinous process. It is advantageously that the suture anchor is implanted within the area of muscle origin or insertion or at least as near as possible. It may be that more than one suture anchor has to be implanted, e.g. in case that more than one muscle has been detached. One end of the suture should subsequently be threaded through the detached muscle or tissue attaching the muscle to the bone (e.g., a tendon) and the other end should be threaded through the corresponding muscle (the same muscle on the other body side) or tissue attaching the muscle to the bone (e.g., a tendon) which may still be attached to the spinous process. Using the threaded suture ends and if necessary an additional tool (tweezers) the detached muscle or muscles can be pulled up to the spinous process. Thereafter the ends of the suture may be knotted on the dorsal side of the reattached one. Nevertheless, it may also be possible to use a knot-free anchor.

Depending on the muscle cut off the spinous process an additional, optional step may be included. Thereby the muscle that has been detached from the spinous process is sewed up with the same muscle on the other side (preferably not being removed from the spinous process) using an additional suture. Therefore, one to five stiches are made linking both muscles or, respectively, the tissues attaching both muscle to the bone.

It is possible to use a wide range of known anchors and suture anchors within the method of the invention. The anchors as well as the suture anchor should be rather small and holding at least one suture with two open ends. Nevertheless, it is advantageously that the anchor and the at least one suture anchor used within the method of the present invention includes a material having thermoplastic properties. The anchors having thermoplastic properties may be anchored in the bone opening with the aid of vibratory energy used for in situ liquefaction of the material having thermoplastic properties.

Therefore, one embodiment of the first aspect of the invention refers to a method, wherein the suture anchor includes a material having thermoplastic properties and is anchored in the bone opening (of the spinous process) with the aid of vibratory energy used for in situ liquefaction of the material having thermoplastic properties. An additional embodiment relates to wherein the osteosynthesis of the spinous process is done using at least two anchors (or pins) including a material having thermoplastic properties and are anchored in the bone opening with the aid of vibratory energy used for in situ liquefaction of the material having thermoplastic properties.

A suture anchor is a small device used during surgical procedures to attach soft tissue, such as ligaments and tendons, to bone. This may be achieved by tying one end of a suture to soft tissue and the other end to a device which "anchors" the suture to the bone. Suture anchors typically are implanted into the bone with at least on suture attached to the anchor. Various techniques of suture attachment have been developed. Most commonly a suture anchor includes an elongate body to which a suture has been attached using an eyelet or the like. Thereby the eyelet is a hole or a loop in the anchor through which the suture passes. Suture anchors may be made of titanium metal, polyether ether ketone thermoplastic, or biodegradable absorbable material. There are many suture anchors on the market today. In general, they can be classified as screw-in and non-screw-in anchors, commonly using an interference fit or positive generated by barbs. A suture is typically an elongate flexible filament, but may take a variety as different thread or thread-like structures, including imitation fibers, lines, and the like. A suture may be a homogeneous or heterogeneous, and may also include a single filament or a composite suture, such as a two or more twisted or woven filaments. In addition, a suture may be made from a wide array of absorbable (i.e., metabolized by the body) or non-absorbable materials known in the art.

Materials having thermoplastic properties suitable for the suture anchor which can be used in the method according to the invention are thermoplastic polymers, e.g.: resorbable or degradable polymers such as polymers based on lactic and/or glycolic acid (PLA, PLLA, PGA, PLGA etc.) or polyhydroxy alkanoates (PHA), polycaprolactone (PCL), polysaccharides, polydioxanes (PD) polyanhydrides, polypeptides or corresponding copolymers or composite materials containing the named polymers as a component; or non-resorbable or non-degradable polymers such as polyolefines (e.g. polyethylene), polyacrylates, polymetacrylates, polycarbonates, polyamides, polyester, polyurethanes, polysulfones, polyarylketones, polyimides, polyphenylsulfides or liquid crystal polymers LCPs, polyacetales, halogenated polymers, in particular halogenated polyolefines, polyphenylene sulfides, polysulfones, polyethers or equivalent copolymers or composite materials containing the named polymers as a component.

One embodiment of the present invention refers to the method for the treatment of spinal stenosis according to the present invention, wherein the at least one anchor is fully made of a bio-degradable material. Another embodiment of the present invention refers to the method for the treatment of spinal stenosis according to the present invention, wherein the osteosynthesis of the spinous process is done using a plate fully made of a bio-degradable material. Specific embodiments of bio-degradable materials are polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209.

Specific embodiments of non-degradable materials are Polyetherketone (PEEK Optima, Grades 450 and 150, Invibio Ltd), Polyetherimide, Polyamide 12, Polyamidell, Polyamide 6, Polyamide 66, Polycarbonate, Polymethylmethacrylate, Polyoxymethylene, or polycarbonate-urethane (e.g. Bionate by DSM, in particular types 65D and 75D). An overview table of polymers and applications is listed in Wintermantel, page 150; specific examples can be found in Wintermantel page 161 ff. (PE, Hostalen Gur 812, Höchst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff (POM—Polyacetal, tradenames Delrin, Tenac, has also been used in endoprostheses by Protec).

The material having thermoplastic properties may further contain foreign phases or compounds serving further functions. In particular, the thermoplastic material may be strengthened by admixed fibers or whiskers (e.g. of calcium phosphate ceramics or glasses) and such represent a composite material. The material having thermoplastic properties may further contain components which expand or dissolve (create pores) in situ (e.g. polyesters, polysaccharides, hydrogels, sodium phosphates), compounds which render the implant opaque and therewith visible for X-ray, or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed. If the device is to be anchored not with the aid of vibration energy but with the aid of electromagnetic radiation, the liquefiable material having thermoplastic properties may locally contain compounds (particlulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% crystallinity); or mixtures of TCP, HA, DHCP, Bioglasses (see Wintermantel). Osseo-integration stimulating fillers that are only partially or hardly degradable, for non-degradable polymers include: Bioglasses, Hydroxyapatite (>90% cristallinity), HAPEX®. Particulate filler types include: coarse type: 5-20 µm (contents, initially 10-25% by volume), sub-micron (nanofillers as from precipitation, preferentially plate like aspect ratio >10, 10-50 nm, contents 0.5 to 5% by volume). Experiments show that liquefaction with the aid of ultrasonic vibration energy allows filling the thermoplastic polymer to a relatively high degree without impairing the capability of the liquefied material to penetrate structures as e.g. the trabecular structure of viable cancellous bone. This fact ensures that anchor loosening is not a problem within the methods of the present invention.

The suture anchor, the pin for fixation of the plate as well as the osteosynthesis plate used in the method according to the invention may consist of any suitable material or material combination (e.g. polymer, metal, ceramic, glass) which material may be bio-resorbable or not bio-resorbable and liquefiable or not liquefiable. Nevertheless, it is advantageous that at least a part (may be the distal part) of the material of the suture anchor is made of a material being liquefiable. Advantageously these materials are not used within the non-bioresorbable or non-biodegradable materials may include surfaces equipped for furthering osseointegration (e.g. per se known surface structures or coatings) where in contact with the bone tissue, in particular if the material of the suture anchor is bio-resorbable or biodegradable and therefore the anchoring function needs to be gradually taken over by osseointegration. Good results have e.g. been achieved with suture anchors of polylactic acid (PLA) filled with Hydroxyapatite or calcium phosphates, in particular of PLLA filled with 60% tricalcium phosphate or PDLLA 70%/30% (70% L and 30% D/L) filled with 30% biphasic calcium phosphate, combined with suture anchors of PLDLLA 70%/30% (70% L and 30% D/L), as available from Bohringer as LR706. In the case of the suture anchor being integrated in the suture anchor, the two items may consist of the same material, e.g. the above named PLLA filled with 60% tricalcium phosphate or PDLLA 70%/30% (70% L and 30% D/L) filled with 30% biphasic calcium phosphate, wherein the filler content may be smaller in areas in which the material is to be liquefied than in other areas.

If the suture anchor is to be forced into the bone, it needs to include at least in its distal end a material having a corresponding mechanical strength which is dependent on the mechanical resistance expected of the hard tissue into which the anchor is to be forced. If such resistance is relatively high (forcing through cortical bone or hard and dense cancellous bone) the distal end of the anchor includes e.g. a metal such as e.g. titanium or a titanium alloy, a ceramic material such as e.g. sintered calcium phosphate (e.g. hydroxyapatite) or engineering ceramics (e.g. zirconia, alumina) or PEEK or a comparable high temperature resistant polymer, while other anchor portions are made e.g. of a biocomposite material such as e.g. the above mentioned filled polylactides or of one of the other above mentioned thermoplastic polymers. Alternatively, such distal end of the anchor may include a hard and possibly abrasive coating e.g. made by plasma sprayed deposition of calcium phosphate or titanium powder on PEEK or polylactide or biocomposites.

The energy used for the liquefaction of the material having thermoplastic properties is preferably mechanical vibration, in particular ultrasonic vibration generated by a vibration source (e.g. piezoelectric vibration generator possibly including a booster to which the tool is coupled) and the anchoring tool is suitable for transmission of the vibration from its proximal end to its distal face, preferably such that the distal face vibrates with a maximal longitudinal amplitude. For the in situ liquefaction the vibration is transmitted from the distal tool face to the suture anchor and transformed into friction heat in places where the suture anchor is held against a counter element (hard tissue and/or part of the suture anchor). It is possible also to activate the anchoring tool to vibrate in a radial or in a rotational direction.

Alternatively, the energy source may be a laser, preferably emitting laser light in the visible or infrared frequency range and the anchoring tool is equipped for transmitting this light to its distal end, preferably via glass fiber. For the in situ liquefaction the laser light is transmitted into the suture anchor and absorbed where liquefaction is desired, wherein the material of the suture anchor may contain particles or substances effecting such absorption.

The hard outer layer of bones is composed of cortical bone also called compact bone being much denser than cancellous bone. It forms the hard exterior (cortex) of bones. Cancellous bone, also called trabecular or spongy bone, is the internal tissue of the skeletal bone and is an open cell porous network. The vertebrae consist of thin layers of compact bone surrounding a spongy interior. Because of the specific properties of the suture anchor and the pins they require little space. It is possible to anchor them in the vertebrae in a way that only one cortex is used but enough strength is provided for the function of the suture. Thus, the present invention refers to methods wherein the suture anchor and/or the anchor used during osteosynthesis are implanted unicortical. Thereby unicortical means that the suture anchor or pin is anchored in a blind hole. Thus, the bone opening for the anchor goes only through one thin layer of the compact bone surrounding the vertebrae. In addition, also the material of the suture anchor after liquefaction and resolidification does not invade the second cortex or layer of compact bone. This ensures that the spinal cord is not hurt. Similar, this is also true for pins implanted in the direction towards the lateral foramina. In this case, the risk of injury of the spinal nerve is minimized.

The suture anchor used is advantageously designed in a way that it can be implanted using a bone opening being shorter than the suture anchor which makes it possible to set a suture anchor within the tip of a small spinous process. Therefore at least a part of the suture anchor, its pin-like structure or the pin should be made fully of liquefiable material. It is advantageous that at least one section of the suture anchor located within its length and including the full cross section of the suture anchor is made of a thermoplastic material to be liquefied. Using such a suture anchor makes it possible to have a short bone opening because the liquefiable material of the suture anchor invades in the surrounding spongy bone tissue. Therefore during implantation the length of the suture anchor shortens but the material of the anchor is distributed within the area surrounding the bone opening. By the same the pulling force to be exerted on the suture increases. The same applies respectively to the pin to be used for osteosynthesis of the spinous process.

In case that the surgeon prefers to detach the muscles on both sides of the spinous process it may not be necessary to cut the spinous process. When using the suture anchors as described above it is even possible to set two anchors at the dorsal tip of the spinous process to reattach the muscles. Because the suture anchors can be adapted to a bone opening shorter that the anchor itself and because the anchors do not weaken the structure of the bone but even make it denser because of the material invading in the spongy structures. Thus, it is possible to use two anchors which intersect. Therefore, two anchors may be located within minimum space such as the spinous process.

Consequently, one embodiment refers to a method for the treatment of spinal stenosis including:
  cutting off a muscle origin or insertion from (each side of) a spinous process
  resecting at least a part of the lamina arcus vertebrae and thereby decompression of the spinal cord within the foramen vertebral
  placing two suture anchors within the spinous process and reattaching the muscle origin or insertion to the spinous process, wherein one suture anchor is located on each side of the spinous process.

Inserting at least one suture anchor into a bone opening and anchoring the at least one suture anchor may include the following steps: Introducing the suture anchor into the bone opening with the suture having two freely accessible ends by pushing the suture anchor into the bone opening using a tool and by simultaneously or later transmitting energy via the tool to the suture anchor thereby liquefying material of the suture anchor having thermoplastic properties. Using the inventive method there is no need to pull the anchor tight to determine whether full insertion has been reached.

The goal of the method for surgical treatment as described so far is to alleviate neural compression (decompression). In selected patients with a deformity or instability, it is necessary to stabilize further the spine (fusion), so as to prevent further spinal compression and recurrent symptoms. Therefore, it may be that in addition to the laminectomy, a spine fusion surgery is also necessary in order to achieve adequate decompression. This is especially true if the nerve root of a spinal nerve is compressed as it leaves the spine, known as foraminal stenosis. The second aspect refers to methods of for spine stabilization. Thereby suture anchors are used to implement a tension band wiring. The goal is to stabilize two articulating vertebrae or to adjust the curvature of the spine formed by these vertebras. Thus, spondylolisthesis (forward displacement) of a vertebra or retrolisthesis (posterior displacement) of a vertebra with respect to the adjacent vertebra should be avoided. Thereby the adjacent vertebra is mostly the uppermost vertebra of spinal fusion. The methods of the second aspect are helpful in connection with spine decompression respectively after laminotomy or laminectomy or in connection with a spinal fusion. The main objective of the methods according to the second aspect is to build a transition zone to bridge a fused segment to a nonfused segment by spreading the forces.

This needs to be carefully differentiated from rigid fixation of the spine, where a fusion is intended. Spinal fusion, also called spondylodesis or spondylosyndesis, is a thereby defined as neurosurgical or orthopedic surgical technique that joins two or more vertebrae into one single structure. Spinal fusion prevents any movement between the fused vertebrae. A soft stabilization or flexible stabilization, as described herein leaves the spinal segment mobile, and its intention is to alter the load bearing pattern of the motion segment, as well as to control any abnormal motion at the segment. The control of abnormal motions and more physiological load transmission should relieve pain, and prevent adjacent segment degeneration. A remote expectation is that, once normal motion and load transmission is achieved, the damaged disc may repair itself, unless of course the degeneration is too advanced.

There is the need for a posterior soft stabilization system promising to add stability after decompressive laminectomy, spinal fusion or facetectomy. Therefore, the second aspect of the present invention describes a new method for introducing a tension-band wire for stabilization of the spine besides the spinous processes. Mostly, the methods involves at least four suture anchors as described above that can be placed in the lamina arcus vertebrae. There may be the rare case that a severe scoliosis indicates for tethering on only one side of the spine. In such a case two (two vertebrae) or three (three vertebrae) suture anchors may be sufficient. In case that four suture anchors are used one suture anchor may be placed per lamina arcus vertebrae and two suture anchors per vertebra. Therefore, at least four suture anchors are used to stabilize the connection of two vertebrae. The method using one suture anchor per lamina arcus vertebrae and side can be suitable to stabilize the cervical spine. Alternatively, one can implant the suture anchors within the pedicle of a vertebrae, which is suitable in thoracic and lumbar spine.

One embodiment of the second aspect refers to a method for spine stabilization including the following steps: positioning of at least one suture anchor per lamina arcus vertebrae of at least two adjacent vertebrae and knotting together suture ends of two anchors located in different vertebras at corresponding locations within the lamina arcus vertebrae. In addition, a fixation within the pedicle of vertebral arch (analogous to a pedicle screw) is possible. This seems to be favorable for stabilization of thoracic vertebrae, where it allows a paraspinal access. Therefore, less muscles has to be detached from the spine. Also, in this case, one suture anchor per side of each vertebra may be enough.

It is also possible to fixate the suture anchors in the spinous process, one on each side. In the cervical spine, it can be sufficient to use only one suture anchor per vertebrae and fix it at the dorsal end of the spinous process. Another location of the suture anchors may be the processus transversus vertebrae. In case that the tension wiring is used to prevent a scoliotic instability it is even advantageously to induce the suture anchors only on one side within the processus transversus vertebrae.

Therefore, another embodiment of the invention refers to a method for spine stabilization including the following steps: positioning of at least one suture anchor per vertebrae of at least two adjacent vertebrae and knotting together suture ends of two anchors located in different vertebras at corresponding locations within the vertebrae, wherein the suture anchor is implanted within the lamina arcus vertebrae, the spinous process, the pedicle or the processus transversus vertebrae. A preferred embodiment of the invention refers to a method for spine stabilization including the following steps: positioning of at least two suture anchor per vertebrae of at least two adjacent vertebrae and knotting together suture ends of two anchors located in different vertebras at corresponding locations within the vertebrae, wherein the suture anchor is implanted within the lamina arcus vertebrae, the pedicle, the spinous process or the processus transversus vertebrae.

For positioning of a suture anchor per lamina arcus vertebrae of at least two adjacent vertebrae (and at least four anchors in total) the surgeon has to drill bone openings into the lamina arcus vertebrae. In the end both lamina arcus vertebrae of all vertebrae to be stabilized should have at least one bone opening. These openings can be blind holes. It is advantageously that the bone openings do not have to reach the ventral cortex (or layer of dense bone). Within these bone openings a suture anchor has to be implanted.

It is also possible to use two suture anchors per lamina arcus vertebrae. Within the thoracic and lumbar spine this is even advantageously. For positioning of two suture anchor per lamina arcus vertebrae of at least two adjacent vertebrae (and at least eight anchors in total) the surgeon has to drill two adjacent bone openings into the lamina arcus vertebrae. In the end both lamina arcus vertebrae of all vertebrae to be stabilized should have two bone openings. These openings can be blind holes. It is advantageously that the bone openings do not have to reach the ventral cortex (or layer of dense bone). Within these bone openings a suture anchor has to be implanted.

It is possible to use a wide range of known suture anchors within the method of the second aspect of the invention. The suture anchor should be rather small and holding at least one suture with two open ends. Nevertheless, it is advantageously the at least one suture anchor used within the method of the present invention includes a material having thermoplastic properties. The suture anchor having thermoplastic properties may be anchored in the bone opening with the aid of vibratory energy used for in situ liquefaction of the material having thermoplastic properties. It is advantageous to use the same anchors as described for the first aspect of the present invention. Therefore, all statements done before in respect to the anchors are also true in regard to the second aspect.

In particular, one embodiment of the second aspect refers to the method for spine stabilization according to the present invention, wherein the anchors are fully made of a biodegradable material. In addition, one embodiment relates to the method according to the second aspect, wherein the suture anchors are implanted only unicortical.

It is further preferred that the suture anchor used within the method of the second aspect of the invention is designed in a way to allow tension or tighten the suture individually. This means the suture may be tensioned in regard to each used anchor independently. This allows to adapt the tension of the suture during the operation to the needs of the patient. For example, it may be advantages to have a higher tension on one side of the vertebrae to correct tilting of the spine (scoliotic tendencies can be compensated). One possibility is to tension the suture by rotation of the anchor. In general, a knot-less fixation of the suture in regard to each suture anchor is preferred. It is preferred that the tension of the suture can be regulated after introduction of the anchor in its bone opening.

One problem that may be occur in regard to the inventive method according to the second aspect is cheese wiring of the suture. Cheese wiring or the cheese wire effect describes the process of suture material cutting or tearing into the bone at the time of suture tension (e.g. by movement of the spine). Depending on the material of the suture, the suture may not cut into the bone but may be damaged by the rim of the bone opening. Both aspects may be reduced or even prevented by a special design of the suture anchors used.

Therefore the present invention also refers to a suture anchor for locking a suture relative to a hard tissue, wherein the suture anchor is designed to be fixed within an opening in the hard tissue and includes a material having thermoplastic properties, for holding the suture, a suture conduit at a distal end of the anchor, and an element for protecting the suture from contact with the hard tissue, in particular from contact to the hard tissue at the rim of the opening respectively at the surface of the hard tissue.

Preferred are suture anchors that allow that the suture can be fixed in regard to the suture anchor in a knot-less manner using the material having thermoplastic properties. For example, to this end, the suture conduit and/or other structure guiding the suture to this end may be collapsible so as to collapse when the thermoplastic material softens during anchoring, or the suture may be weldable to the thermoplastic material.

In many embodiments, the element for protecting the suture from contact with the hard tissue should be suitable to avoid cheese wiring but does not conflicting with curvature of the spine.

The element for protecting the suture from contact with the hard tissue may be an element integrated in a one-piece suture anchor or it may be a separate element (separate from an anchor body that for example has a pin portion).

An element integrated in the one-piece structure may for example include a proximal lateral protrusion (process) that serves as a kind of head portion and through which the suture is guided (channel, for example being a through opening) so that the head portion prevents any direct contact between the rim of the opening and the suture. The head portion in this may be circumferential (flange-like) or include a plurality of protrusion around the periphery of the proximal end of the anchor. It may include one or two (or possibly more) channels for the suture. If the head portion is not circumferential, then instead of being formed by a through opening the channel may also be formed in a notch-like manner.

In case that it is a separate element, it is preferred that the element for protecting the suture from contact with the hard tissue can be rotated within the opening in the hard tissue.

It is further preferred that the suture anchor or its pin portion and the element for protecting the suture from contact with the hard tissue can be rotated independently from each other.

The element may be designed in a way that it has a minimal radial extension, so that, for example, at least 2-3 mm from the opening in the hard tissue the element is located between the hard tissue and the suture.

This means that the suture, protruding out of the combination of the suture anchor and the element for protecting the suture from contact with the hard tissue, lays or runs over the element.

The element for protecting the suture from contact with the hard tissue can be selected from the group including or consisting of: a sleeve traversing the rim of the opening within a hard tissue being designed to fit to the proximal end of the suture anchor; a disc or plate being rotatable in respect to the anchor having at least one channel for the suture, and a process (lateral protrusion) traversing the rim of the opening within a hard tissue and including a channel for the suture and/or extending over the tissue proximally of the rim. The sleeve traversing the rim of the opening within a hard tissue being designed to fit to the proximal end of the suture anchor may have at least one channel for the suture. Alternatively, the suture can protrude out proximal of the suture anchor using a central channel in the sleeve which may be used for a tool and/or for introduction of an element made of the thermoplastic material. In this case, the sleeve may consist of a cylindrical distal end fitting to the proximal end of the suture anchor and being suitable to be introduced into the bone opening. The sleeve may further include a proximal part attached to the cylindrical part in an angle (preferably of 70° to 110°) so that the rim of the bone opening is covered.

The element for protecting the suture from contact with the hard tissue and in particular the disc or plate being rotatable in respect to the anchor having at least one channel for the suture is preferably made of a material being flexible so that it can bend. One suitable material is a thermoplastic polymer foil. This foil may have a thickness of 0.2 to 1.5 mm. It is preferred that the thickness is <1 mm in case that the Young's module is <0.5 GPa and the thickness is <0.5 mm in case that the Young's module is >0.5 GPa.

The disc and the sleeve may be rotational symmetric (round), elliptic or can be nearly rectangular. It is possible that the disc or sleeve extend more to one side of the suture anchor and respectively the bone opening. Depending on the usage of the suture anchor, it can have only one process or two processes being attached on opposite sides of the anchor. Respectively, the sleeve or the disc can have one or two suture channels. This depends on the suture path. In case that the suture runs only to one adjacent suture anchor (and vertebra) it has only one protrusion or channel but in case that the suture runs further to two different vertebrae (suture anchors) one being more cranial and the other one more caudal and therefore in two directions, the element for protecting the suture from contact with the hard tissue should have at least two suture channels or consist of two protrusion with one suture channel each.

The element for protecting the suture from contact with the hard tissue may have a diameter (or a radial extension, possibly measured from the suture anchor body outward) of 1.5 to 10 mm, preferable of 2 to 5 mm and a thickness (dimension from the bone to the suture) of 0.1 to 2 mm, preferably 0.2 to 1 mm, and more preferably of 0.3 to 0.7 mm. In case that the element for protecting the suture from contact with the hard tissue is too large, it causes problems concerning bending and curvature of the spine.

In the second step of the method according to the second aspect suture ends of two anchors are knotted together. Therefore, one suture end of the first anchor is knotted with a suture end of a second anchor and the second suture end of the first anchor is knotted with the second suture end of the second suture anchor. It is advantageously to do this in a way that two parallel sutures run from one anchor in the first vertebrae to another anchor implanted within the adjacent vertebrae. In this case, the sutures should also run approximately parallel to the spine. The sutures may also run diagonally (crisscross). It is preferred that the sutures of two anchors are knotted, wherein the anchors are located at approximately the same position within adjacent vertebrae. Thereby the sutures should be tensioned. Thereby the tension can be adapted individually, also individually per side in a way that scoliotic tendencies can be compensated. It is also possible that two or even more anchors located at approximately the same position within adjacent vertebrae attach only one (continuous) suture to the spine. In this case, the second step of the method according to the second aspect refers to knotting the ends of the suture together, wherein anchors located at approximately the same position within adjacent vertebrae include only one suture and one suture end protrudes of a first anchor is knotted with a suture end protruding of a second anchor. It is preferred that the suture ends to be knotted protrude from the anchors being having the greatest distance from each other. In other words, the one suture attached to several anchors is knotted by knotting the suture end protruding from the highest anchor (anchored in the highest/most cranial vertebra involved) and the suture end protruding from the lowest anchor (anchored in the lowest/most caudal vertebra involved) wherein the anchors are located at approximately the same position within adjacent vertebrae The method according to the second aspect of the invention may also include stabilization of the spine regarding more than two adjacent vertebrae. This is particularly possible when using suture anchors allowing adjustment of suture tension after introduction into the bone opening. Therefore, one suture may be attached to the vertebrae using more than two anchors.

Therefore, another embodiment of the invention refers to a method for spine stabilization including the following steps: positioning of at least one suture anchor per vertebrae of at least three adjacent vertebrae and knotting together the suture ends of two anchors located in different vertebras at corresponding locations within the lamina arcus vertebrae, wherein the suture anchor is implanted within the lamina arcus vertebrae, the spinous process, the pedicle or the processus transversus vertebrae. In the second step of the method according to the second aspect the suture ends of two anchors are knotted together. Therefore, one suture end of the first anchor is knotted with a suture end of a second anchor and the second suture end of the first anchor is knotted with the second suture end of the second suture anchor.

One suture anchor suitable for the method according to the second aspect of the invention is described in EP 2 667 790 (FIG. 12). When using this anchor or any other anchor which is rotated to adapt suture tension, it is preferred that the suture anchors are introduced into the bone openings with a suture loop with the length of 1 to 2 rotations around the anchor between two anchors. When using three or more suture anchors holding one suture, it can further be advantageously to fixated first the anchor in the middle and then the anchor more cranial and more caudal.

The suture of the used suture anchor may be made of any commonly used material. Suitable are e.g. nylon, polyester, PVDF and polypropylene. The sutures must be strong enough to hold the force on the vertebrae securely but flexible enough to be knotted and they must be hypoallergenic. It is preferred to use a flexible suture (e.g. DYNACORD® made of two outer sheaths of braided fibers and a core of silicone and salt). The advantage of these flexible suture is that they respond to changes in tension that occur over time to promote stability. In particular, the combination with the suture anchors to be fixed using vibration is advantageously, because these anchors fixed by form closure show no creep tendency.

A posterior soft stabilization system introduced according to a method of the second aspect promises to add stability to the area of spine above fused vertebrae. Therefore, one embodiment of the second aspect refers to a method, wherein the lower of the adjacent vertebrae to be stabilized is joined to the vertebrae further down by spinal fusion method. This is in particular important within the thoracic or lumbar spine. In connection with the cervical spine this method is rather important in combination with laminotomy or laminectomy. This means that the suture anchors introduced according to a method of the second aspect are used to stabilize vertebrae after laminotomy or laminectomy or to adjust a defined lordosis. It may be the aim of the method to induce a defined kyphosis resp. lordosis or to prevent a progressive, further kyphosis by a rotation or the spondylolisthesis. Therefore, the method of the invention aims for stabilization (in the medium to long term) stabilization by achieving the formation of ligament-like structures or shortening of ligaments. Therefore, the sutures may be supported by graft tissue, such as allografts (like dermograft), autografts or even textile patches.

Spinal fusion is commonly performed together with rigid instrumentation to treat various lumbar spine disorders. Current methods of fixation include posterior pedicle screw instrumentation with posterior lumbar interbody fusion (PLIF) or transforaminal lumbar interbody fusion (TLIF), posterior pedicle screw instrumentation with anterior lumbar interbody fusion (ALIF), and anterior plate and screw instrumentation with ALIF. Over the past 20 years, PLIF with pedicle screw instrumentation has gained popularity in the spine community, and may therefore be considered a standard for fusion to which alternative treatment methods can be compared. Consequently, the second aspect of the present invention refers to methods, wherein the fusion is supplemented with hardware (screws, plates, rods).

The methods of the second aspect may further be useful to create or recreate a posterior tension band. The posterior tension band is part of the spine's anatomy found at the back of the spine (posterior). Elements that make up the posterior tension band are the spinous processes and lamina (bony plate that is part of each vertebral body) along with the ligaments that join these. Often, these posterior elements are removed during a spinal decompression procedure, which can potentially destabilize the spine. Dynamic stabilization restores the posterior tension band (posterior support) without the need for spinal fusion. Therefore, one embodiment refers to a method, wherein the knotted sutures are augmented using an artificial ligament such as a tissue graft which may be attached to the suture. The suture and the tissue graft should be attached in a way that the tissue graft overlays the structure of the suture.

Thereby the suture can provide primary stiffness and the graft takes over stiffness over time. Depending on the material, the stiffness of the suture may decrease (in case that the suture is bioresorbable) and at the same time the stiffness of the graft material will increase because of ingrowing collagen which is forming a composite material. The suture may be combined with a tissue graft made of a poly filament mesh. This mesh can be attached to vertebrae using suture anchors as described herein, in particular, it may be attached to the bone using the anchors fixating the suture, too. In general, the artificial ligament being made of a polyfilament mesh can be attached to the bone using a small pin including or made of a material having thermoplastic properties.

The polyfilament mesh can be a textile material such as a mono fibrillary structure, which may be in the form of woven, knitted, braided or nonwoven fabrics. It is preferred that the polyfilament mesh is made by embroidering. It is preferred that the polyfilament mesh has a loop structure. The fabrics may be made from PET, PTFE or polyamide fibers. Additionally, a portion of the fibers or all may be made from a slowly resorbable polymer (poly-L-lactid acid, poly-hydroxy-alkanoate (e.g. buturate)) to gradually reduce stress shielding on the forming collagen fibers to train the establishing fibrous tissue to maximum strength.

A polyfilament mesh and the ingrowth of collagen may cause scar formation which may form unwanted adhesions. Therefore, it is preferred that the artificial ligament being made of a polyfilament mesh includes further at least one membrane. Therefore, the tissue graft may consist of a porous membrane and a textile structure, which is located in the direct proximity of said membrane. Thereby the membrane may be attached to the side of the artificial ligament showing to the nerve. An alternative embodiment of the used tissue graft may be made of two porous membranes and a textile structure between these membranes. Thereby the textile structure can be a polyfilament mesh as described before. The membrane protects from formation of adhesions. The membranes can be elastic. The membranes can have pores. It is preferred that the pores have a diameter between 1 and 5 mm. This allows that blood can be introduced and that blood vessels can ingrowth into the textile structure. It may further be advantageously that only one membrane has pores or that the pores of a first membrane have a larger diameter than the one of the second membrane. In this case, the graft tissue should be implanted in a way that the membrane without pores or the second membrane is located towards the bone. A graft tissue with membranes has the advantages that blood vessel growth in increase because of the reduces partial oxygen pressure between the membranes or respectively within the textile structure. In the following the formation of tendinous, connective tissue and collagen formation is promoted.

Thus, the stiffness is finally built by a composite of graft tissue and collagen built by ingrowing cells of the patient. Therefore, particularly suitable is a graft material supporting ingrowth of cells. This is different to many other applications of graft tissue where an increase in stiffness is not wanted (hernia meshes). The U.S. Pat. No. 6,737,149 B1 describes a graft material wherein materials with the hierarchy of pores as described in FIG. 2 of U.S. Pat. No. 6,737,149 B1, namely elements 14, 24 and 34 are suitable to be used within the present invention. It could be shown that these materials are able to attract appropriate vascularity and by this support the formation of a neo-ligament. The stimulation points 13 described in U.S. Pat. No. 6,737,149 B1 however are of harm for a use within methods of this invention since they would create mechanical irritation and uncontrolled scar formation towards the nerves nor towards the muscle tissue.

The methods according to the second aspect of the invention results in dynamic stabilization of the spine. The resulting system of sutures and optionally artificial ligaments may be defined as a system, which would favorably alter the movement and load transmission of a spinal motion segment, without the intention of fusion of the segment.

The present invention includes a third aspect. This third aspect refers to methods for reduction of unwanted effects after spinal treatment. The human spine is meant to curve slightly at various points to help absorb shock and distribute stress safely through the spine. The natural curves of the spine, which occur in the neck, torso and lower back, also position the head above the pelvis. However, when the spine curves in too much, it results in a condition called lordosis (hydrolordosis) or swayback. This can cause a number of undesirable side effects, also regarding surgical spinal treatment. The lordosis may cause a detachment of muscles from the lamina of the vertebra arch which results in an empty space. During surgery the patient is lying which reduces the lordosis of the spine and the empty space. After or during surgery of the spine the empty space is increasing and can be filled with liquid. Edema or bleeding may be the result. To avoid the empty space or to reduce it, a suture anchor may be inserted into the lamina of vertebral arch or its processes. The suture may be used to pull the muscle to the vertebra. Alternatively, the suture may be used to hold or attach a wire or strap which pulls the muscle to the bone.

Therefore, another embodiment of the invention refers to a method for spine treatment including the following steps: positioning of at least one suture anchor into a lamina of a vertebral arch or one of its processes and pulling muscles to the vertebrae, wherein these muscles have been detached from the vertebrae because of lordosis. In other words, another embodiment of the invention refers to a method for spine treatment, in particular for reduction of empty space between bone structures of a vertebra and a spinal muscle, including the following steps: positioning of at least one suture anchor into a lamina of a vertebral arch or one of its processes and pulling at least one muscle to the vertebra in order to reduce an empty space between the respective vertebrae and the pulled muscle caused by lordosis. The step "at least one muscle to the vertebra" includes usage of a wire or strap that embraces the at least one muscle or parts of the at least one muscle and is attached to the bony structure of the vertebra by the suture anchor.

It is possible to use a wide range of known suture anchors within the method of the third aspect of the invention. The suture anchor should be rather small and holding at least one suture with two open ends. Nevertheless, it is advantageous that the at least one suture anchor used within the method of the present invention includes a material having thermoplastic properties. The suture anchor having thermoplastic properties may be anchored in the bone opening with the aid of vibratory energy used for in situ liquefaction of the material having thermoplastic properties. It is advantageous to use the same anchors as described for the first and second aspect of the present invention. Therefore, all statements done before in respect to the anchors are also true in regard to the third aspect.

DETAILED DESCRIPTION OF THE INVENTION

The following more detailed description of the embodiments of the method is a representative of exemplary embodiments of the technology, wherein similar parts are designated by same numerals throughout. Standard medical planes of reference and descriptive terminology are employed in this specification. A sagittal plane divides a body into right and left portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Proximal means toward the trunk, or, in the case of an inanimate object, toward a user. Distal means away from the trunk, or, in the case of an inanimate object, away from a user. Dorsal means toward the top of the foot. Plantar means toward the sole of the foot. Ipsilateral means on the same side of the body. Contralateral means on the opposite side of the body.

Figure 1:
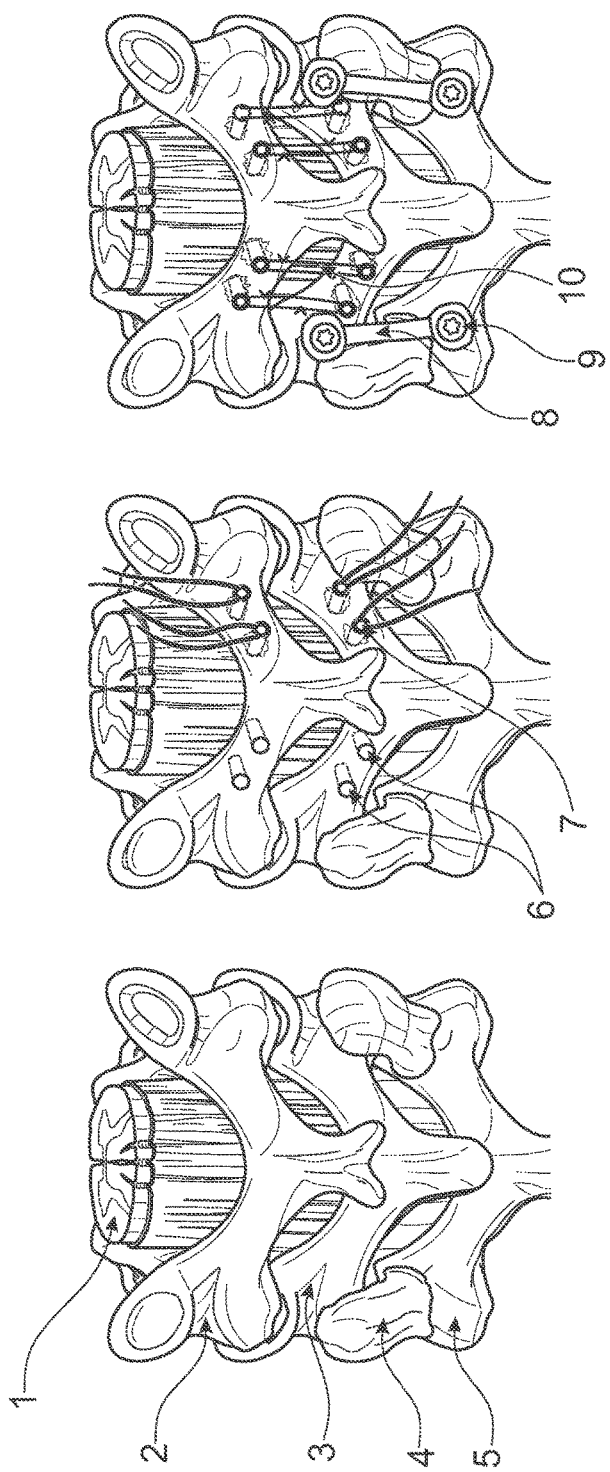
FIG. 1 shows a schematic overview of the method according to aspect 2 according to the present invention.

FIG. 1 illustrates the method according to aspect 2 of the present invention. Exemplarily, the method is shown at the cervical spine. The figure shows a fusion of the first thoracic vertebra 5 with vertebra prominens 3, the seventh cervical vertebra, which are shown with the spinal cord 1 and the articular capsule 4. Therefore, pedicle screws 9 together with a fusion rod 8 are used. The articulation between the seventh cervical vertebra 3 and the sixth cervical vertebra 2 is stabilized by a tension band wiring according to the second aspect of the invention. In a first step two bone openings 6 are made in each lamina arcus vertebrae of each vertebrae, therefore in total eight bone openings 6 are introduced. These openings do not have to be through holes.

It is sufficient that only the proximal cortex of the lamina is opened up by drilling. It is shown in FIG. 1 that the bone openings are made before the fusion is established but this is not necessary, the openings may also be drilled after the fusion is established. Subsequently in each bone opening a suture anchor is fixed 7. Thereby it is important that the anchors used can be fixated unicortical. The anchors may be fixed by liquefying a thermoplastic material of the anchors using oscillation. The liquefied material is displaced into the pores of the surrounding bone. Therefore, the bone opening can be shorter than the anchor. During fixation the anchor shortens depending on the amount of thermoplastic material liquefied. Therefore, the user may adapt the length of the anchor after implantation to the individual vertebrae and circumstances. The anchor has enough strength for the bracing also in case that it is fixed only in an opening of minimal length (1.5-3 mm). It is suitable to use very small anchors such as the SportWelding® Fiji Anchor®.

Figure 3A:
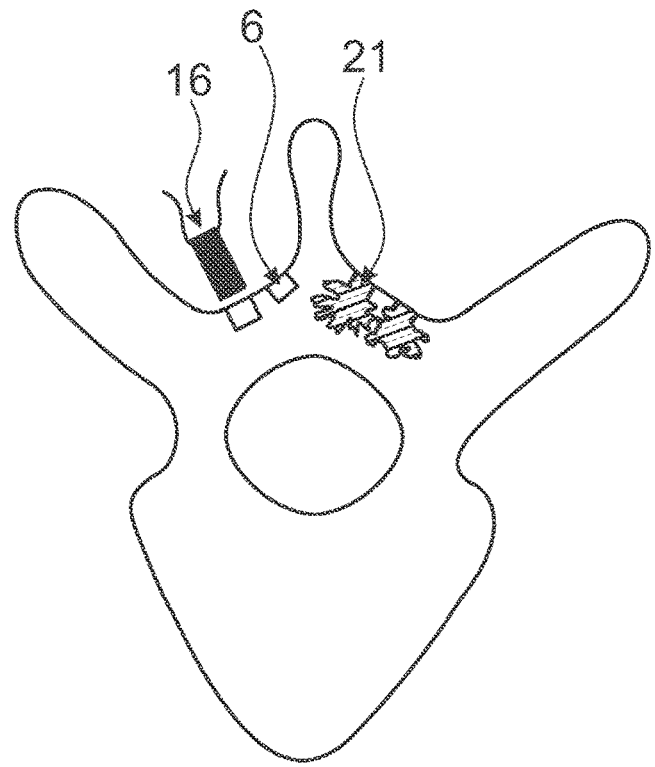
FIG. 3 shows a schematic view of a thoracic vertebrae having openings with and without suture anchors for the method according to aspect 2 of the present invention.
Figure 3B:
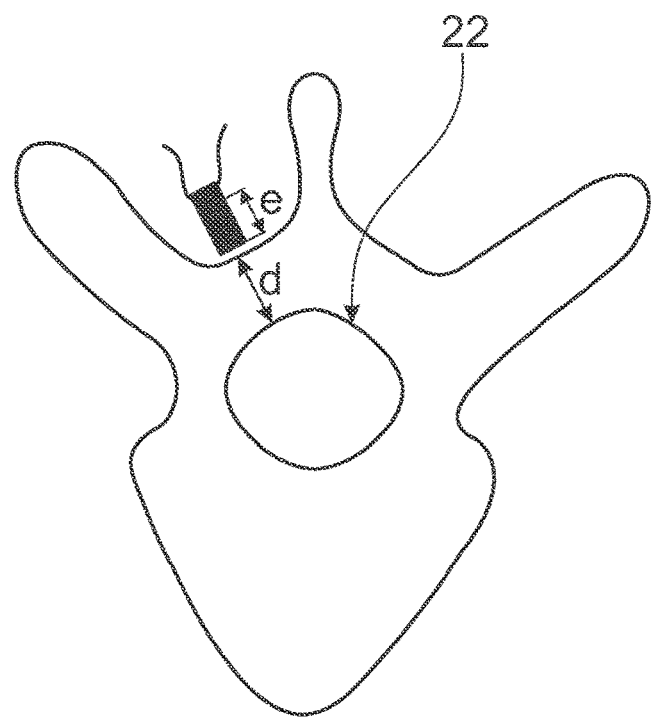

FIG. 3 shows a schematic view of the sixth thoracic vertebrae cut in transverse plane. In the vertebrae shown in FIG. 3 a) the lamina arcus vertebrae on the left side has two bone openings 6. Furthermore, a suture anchor 16 before implantation is shown. The lamina arcus vertebrae on the left side shows two anchors after fixation (not shown are the sutures of these anchors). One can see that the liquefied material 21 of the anchors has been filled the pores of the cancellous bone within the lamina arcus vertebrae. This ensures the strength of the anchoring. The width d of the lamina arcus vertebrae as shown in FIG. 3 b may be smaller than the length e of the anchor (d<e). In particular d may be between 4 to 5 mm and e around 7 mm. The opening used to implant the anchor is preferably even less than the width d. Therefore, the method of the present invention is able to protect the spinal cord because the distal cortical end of the lamina arcus vertebrae 22 stays intact (the bone openings 6 are no blind holes). This enables to treat also fragile vertebrae or vertebrae with small laminas (cervical spine) using the method of the present invention.

In the last step the bracing is finalized by knotting the sutures 10. Therefore, the suture ends of two anchors being located in opposite openings on neighboring vertebrae are linked by two knots. This results in two double stranded links for each lamina arcus vertebrae. The strands or knotted sutures 7 of one pair of anchors run essentially parallel to each other.

FIG. 2 illustrates the method according to aspect 1 of the present invention. Said method refers to a method of laminotomy or laminectomy. Shown is exemplarily a lumbar vertebrae 20. In a first step the muscle insertion or the muscle origin 11 (depends on the vertebrae to be treated) of the autochthonous back muscles at the spinous process 12 are cut. It may be that only one origin or respectively insertion has to be cut to get enough space to reach the basis of spinous process and the area of the lamina arcus to be treated. Deepening on the vertebrae it may also be that more than one muscle inserts or origins 11 at the respectively spinous process 12 and has to be cut. In FIG. 2a) is shown that the origin of the longissimus has to be cut. The cut should be as close to the bony structure as possible. The method according to the invention has the advantage that only the muscle insertion/origin of one side has to be cut. Thereafter (FIG. 2b) the muscles filling up the groove on the side of the spinous processes of the vertebrae (here the multifidus muscle consisting of a number of fleshy and tendinous fasciculi) can be pushed so that it is possible to cut away the spinous process 12 at its basis or transition to the lamina arcus vertebrae. The cut 13 at a frontal or coronal plane of the vertebrae separates the spinous process from the vertebrae. Said cut 13 allows to pushes away the spinous process 12 together with the muscles attached thereto. In the subsequent step (FIG. 2c) a partial resection 14 of the lamina arcus vertebrae is carried out. This partial resection may be enough to result in the wanted decompression of the spinal cord. Nevertheless, it may be necessary to introduce a tool 15 which allows to ablate degenerative alterations, such as osteophytes within the foramen vertebral (decompression of the spinal cord) or the foramen intervertebral (decompression of the spinal nerves and arteria vertebral).

Thereafter (step shown in FIG. 2d) the spinous process may be relocated and fixed to the vertebrae. It is preferred to use a plate 17 made of biodegradable absorbable material which is fixed using two pins or anchors 16 made of thermoplastic material. These pins 16 can be liquefied using oscillation. As described for the anchors above the liquefied material invades in the porous structures of the cancellous bone and thus anchors the plate. The plate has to be fixed to traverse the cut 13 of the spinous process but does not need to reach the partial resection of the lamina arcus vertebrae.

In the following step at least one suture anchor 7 has to be placed within the spinous process. It may be that more than one anchor is necessary or at least suitable e.g. in case that more than one muscle insertion or origin has been cut on the respective side of the spinous process. It is preferred that the anchor is set in a way that it is within the area of the muscle origin or insertion of the muscle to be fixed. In this case the muscle can be fixed directly to the bone which is infringed by the opening which is a suitable stimulus for recruitment of reparative cells and genes. Therefore, it is helpful for the reattachment of the muscle that the anchor is placed directly within the area of muscle insertion or origin. This should be possible also for narrow spaces because the anchors are short and can be set within a bone opening being even shorter, see FIG. 3.

One end of the suture of the suture anchor 7 is threaded through the muscle insertion or origin not cut off from the spinous process and the second end of the suture is threaded through the tendon or of the muscle or the muscle itself which has been cut off from the spinous process. With the help of the suture ends the muscle that has been cut can be pulled back to the spinous process and can be attached to the spinous process and the corresponding muscle on the other side of the spinous process. Finally, the ends of the suture are knotted as shown in FIG. 2g). The knot 19 of the suture is located on the tendinous insertion or origin of the muscle respectively on the dorsal side of the muscle.

Figure 2B:
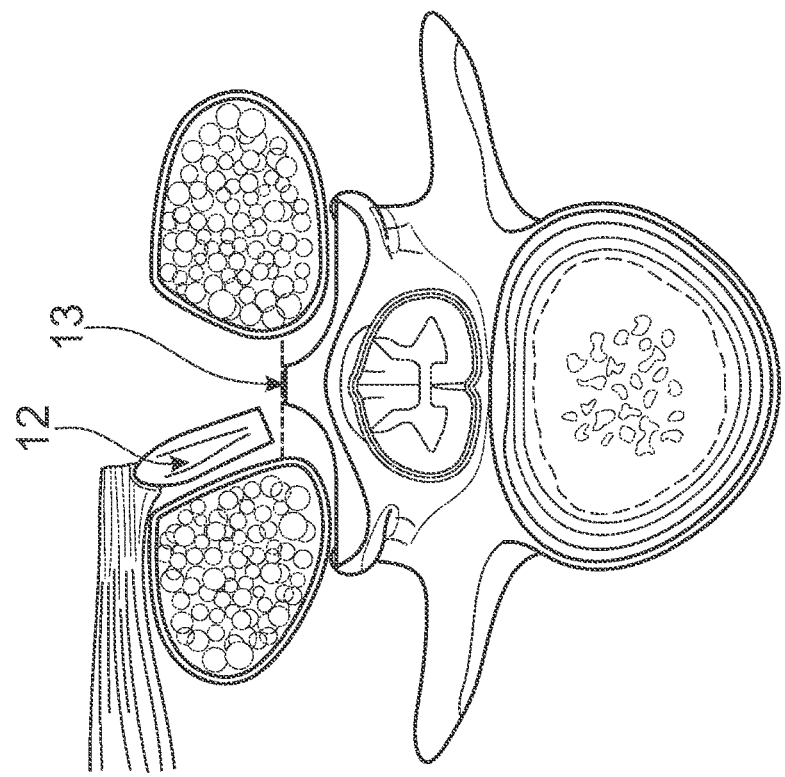
FIG. 2 shows a schematic overview of the method according to aspect 1 of the present invention.
Figure 2A:
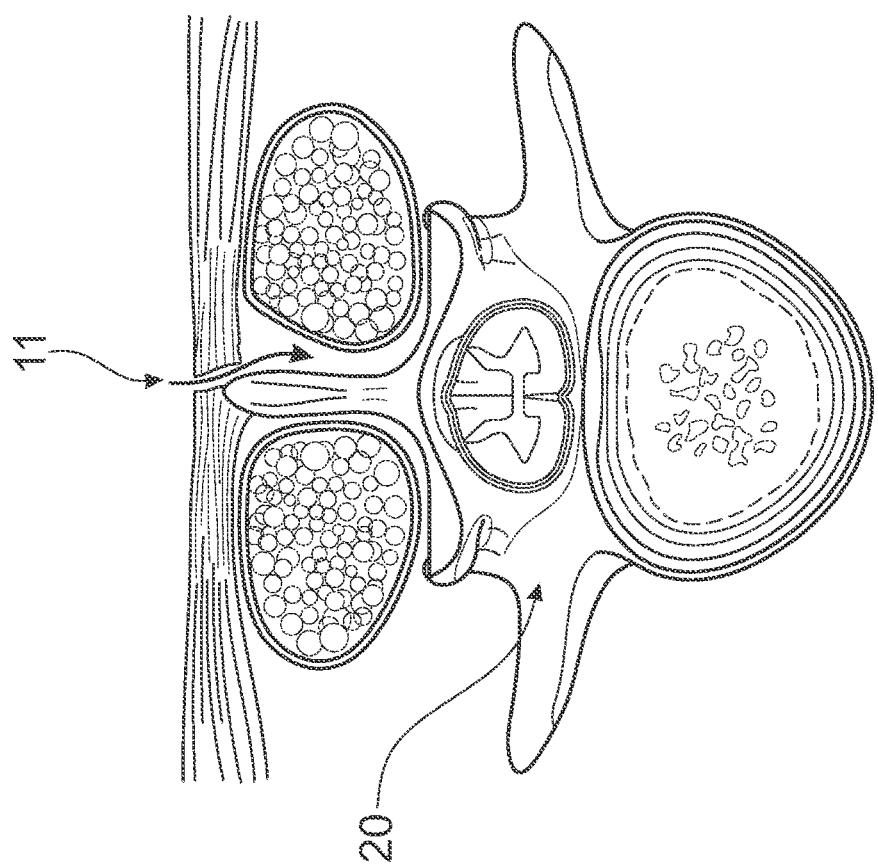
Figure 2C:
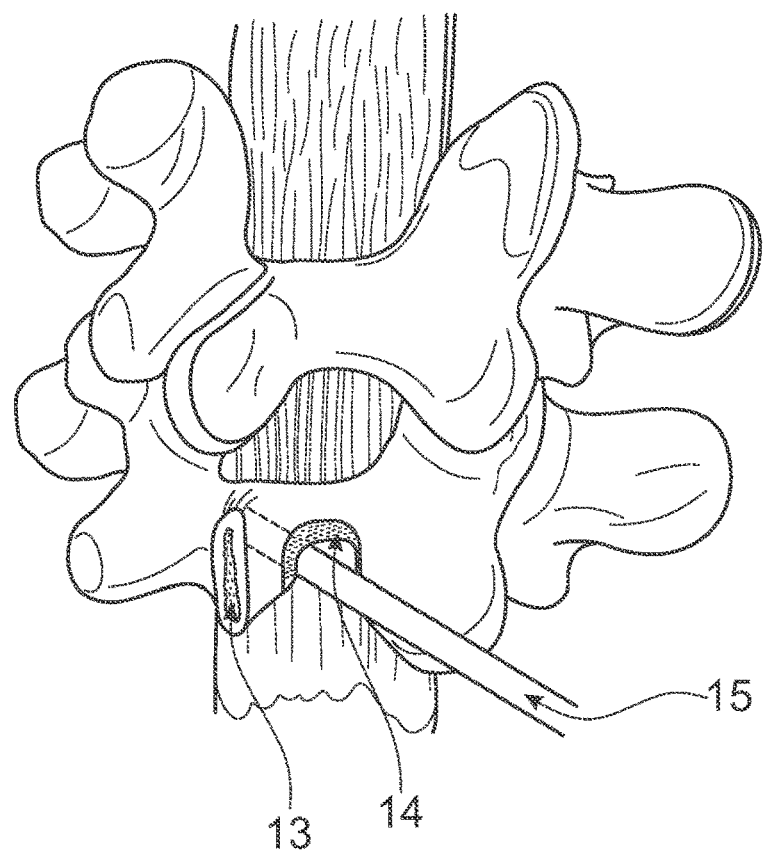
Figure 2D:
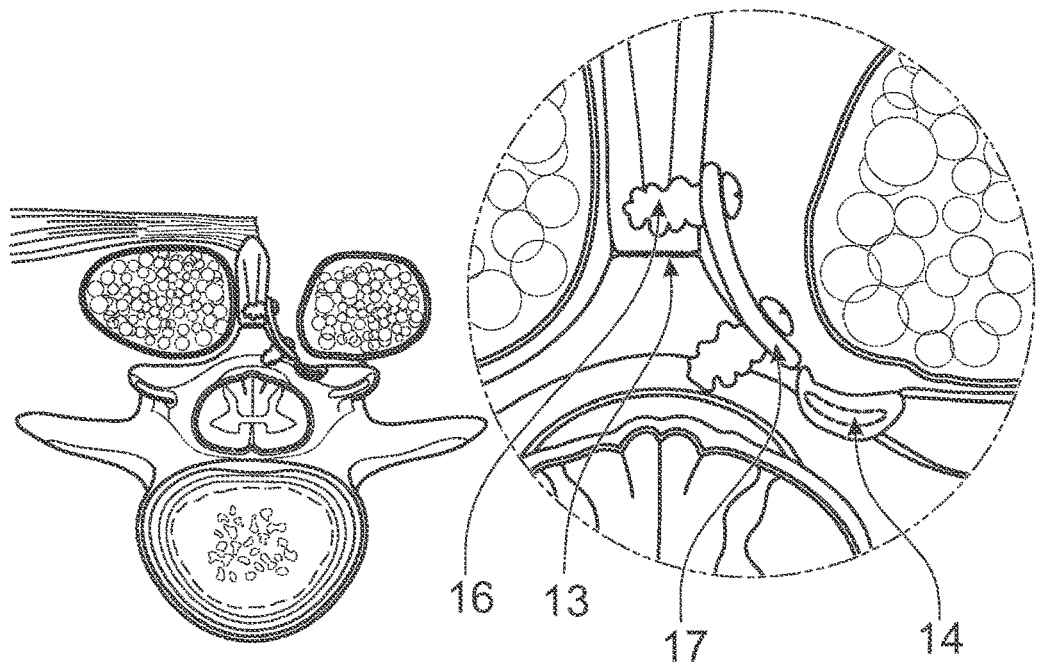
Figure 2E:
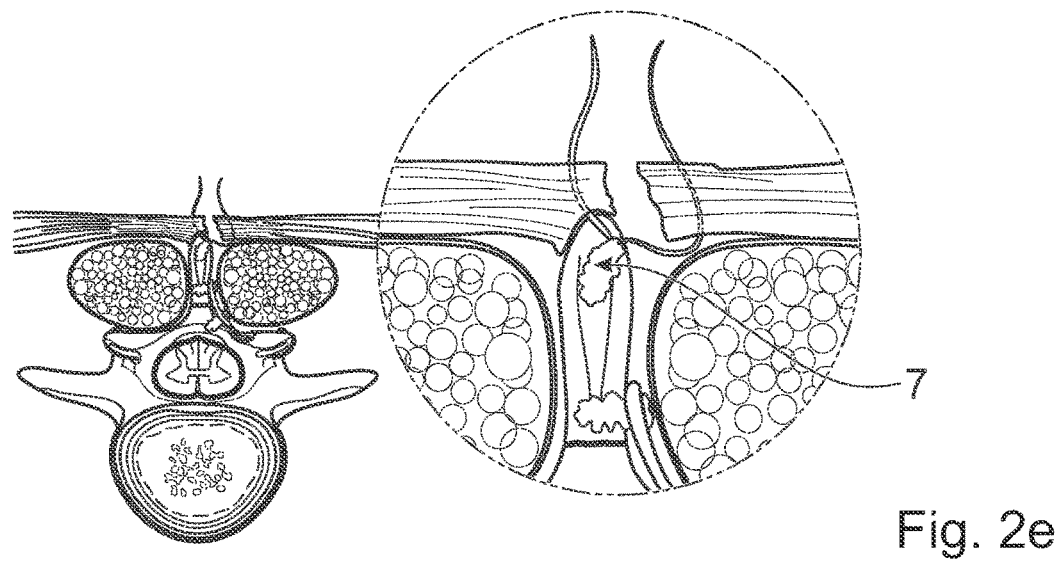
Figure 2F:
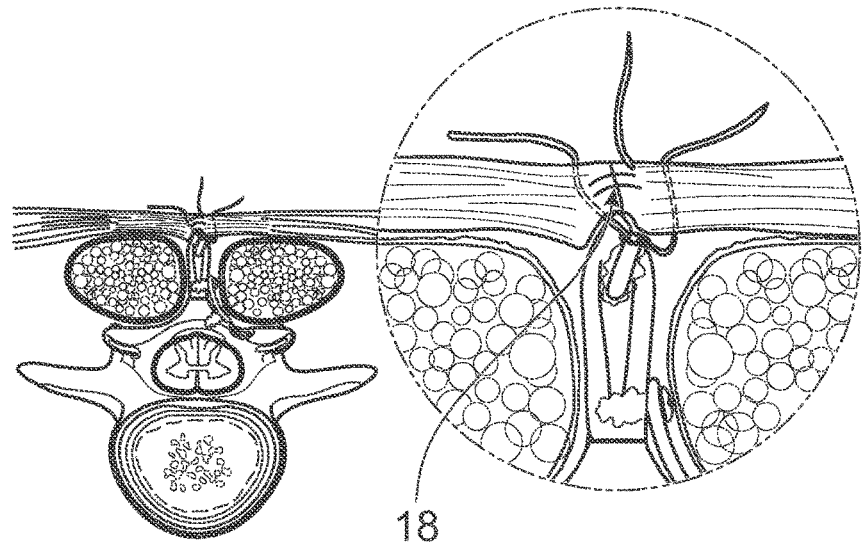
Figure 2G:
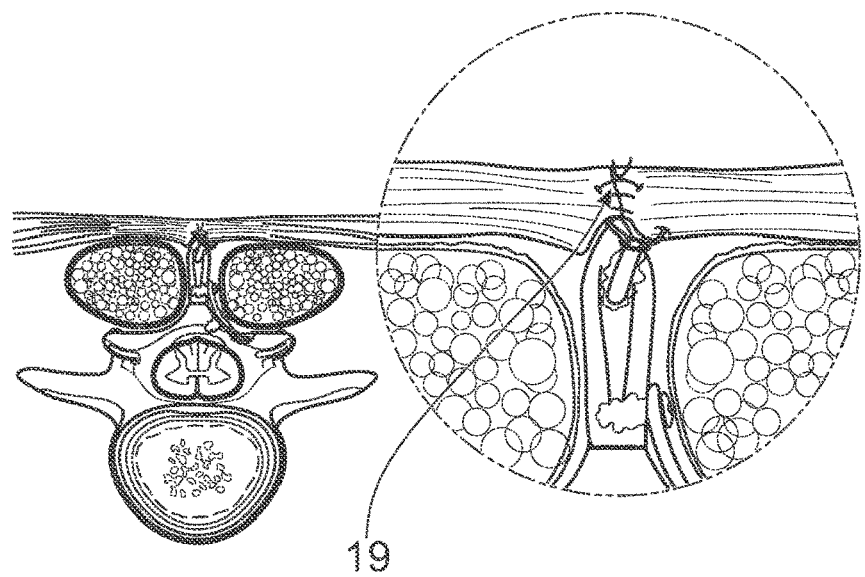

FIG. 2f) shows an optional step of the method. In addition, to the reattachment of the muscle to the bone and the corresponding muscle of the other side using the suture of the suture anchor 7 it may be suitable to use an additional suture 18 reattach the muscle to the corresponding muscle of the other body side. This is done by simple stitching to sew the muscle being cut off to the corresponding muscle which stayed on the spinous process.

Figure 4:
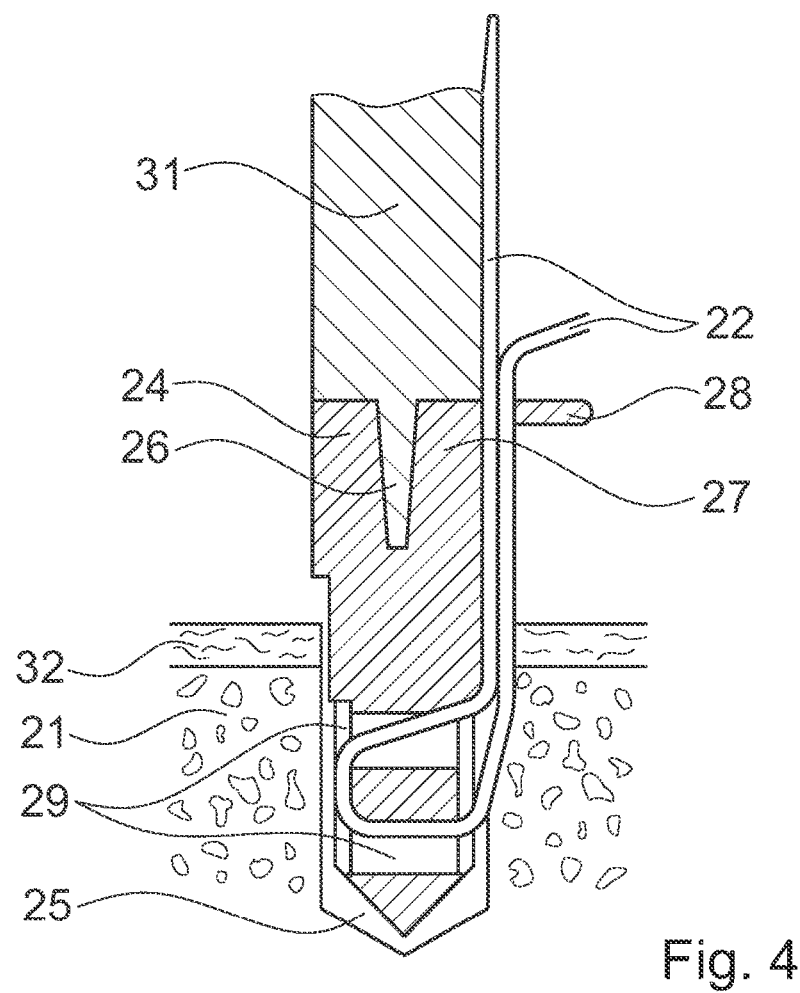
FIG. 4 shows a schematic view of an anchor according to the invention. The anchor has at least one element to protect the suture from contact with the rim of the bone opening.

FIG. 4 shows an exemplary embodiment of the suture anchor according to the invention, which is especially designed to be used within the methods according to the invention. This suture anchor 24 include a material having thermoplastic properties (liquefiable material) or is preferably made of such a material and can be anchored in a hard tissue opening 25 by in situ liquefaction of at least part of the material having thermoplastic properties and by making the liquefied material to flow into the hard tissue to constitute, when re-solidified, a positive fit connection between the anchor and the hard tissue 21. The anchoring method on which the anchors according to the invention are based is disclosed e.g. in the publication U.S. Pat. No. 7,335,205 the disclosure of which is enclosed herein in its entirety. According to this method, a proximal face 26 of the anchor is contacted with a tool 31 which transmits energy into the anchor, in particular a vibration tool which transmits vibrational energy. Simultaneously the anchor can be pushed into a hard tissue opening.

Furthermore, the suture anchor according to FIG. 4 includes at least one distal suture conduit 29 (e.g. distal groove, channel, or eyelet) in which the suture is held when the suture anchor is positioned relative to the hard tissue opening and fixated therein, e.g. by collapsing the suture conduit and such braking or clamping the suture threaded there through.

The suture anchor 24 as shown in FIG. 4 includes a pin portion and advantageously a head portion 28 and is shown attached to a tool 31, by e.g. a press fit connection between a tool protrusion reaching into a recess in the head portion. At least the pin portion includes at least at parts of its lateral surfaces the material having thermoplastic properties. The head portion 28 may also include a suture channel 27, for example including a through opening. The suture 22 is preferably threaded there through and through the groove 29 in a way that the suture 22 can be adjusted after positioning of the suture anchor within the hard tissue opening 25. After adjustment of the suture length and/or the suture tension the suture can preferably be fixated without a knot, e.g. by collapsing the suture conduit or channel during liquefaction of the thermoplastic material.

The head portion 28 of the suture anchor may consist of one or two or more process(es), especially protruding laterally at a proximal position, having a channel for the suture 22. According to an option, the head portion is formed by a circumferential flange that has one or two (or possibly more) of the channels being through openings.

The process may be located out of the hard tissue opening 25, especially proximally thereof. This allows that the suture 22 is prevented from direct contact with the bone tissue around the opening—it may for example rest on the process after fixation. This measure serves for preventing damage of a friction sensitive suture. The rim of the hard tissue opening can be rather sharp. During movement of the spine by the patient the forces affecting the suture are high. Therefore, the suture may be damaged when rubbing on the wall of the hard tissue opening. In addition, the head portion may be used to clamp, to position or to fix an artificial tissue 32.

The pin portion may include two suture grooves 29 running across the distal pin face so that the suture 22 can be threaded as a loop 23. In axial direction, the suture can further run along one or along two opposite anchor sides.

The head portion 28 has a larger cross section than the distal end of the hard tissue opening 25 such that, when the anchor is positioned within the opening, the head portion or at least one process of the suture anchor at the proximal face protrudes beyond the proximal end of the opening at least on those side or two sides on which the suture 22 reaches this proximal anchor face.

Figure 5:
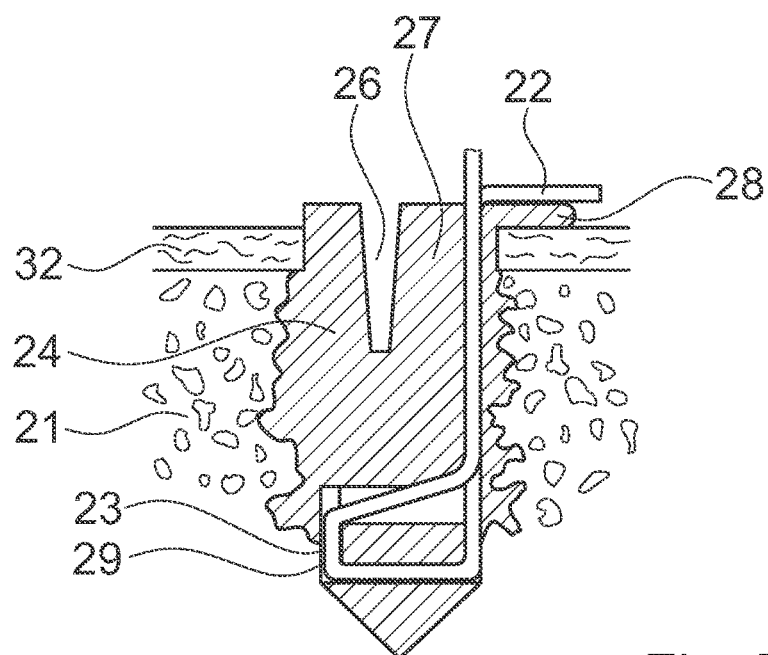
FIG. 5 shows a schematic view of the anchor according to FIG. 4 after anchoring in a bone opening.

For fixating a suture 22 relative to hard tissue 21 using the anchor as illustrated in FIGS. 4 and 5, a hard tissue opening 25 is provided. The pin portion 24 of the anchor, which is attached to the tool 31 being coupled to an energy source (preferably vibration source), is positioned into the mouth of the opening 25, the suture to be fixated by the anchor running through the suture grooves 29 and extending out of the hard tissue opening through channel 27 of the anchor head. A force is then applied to the suture anchor via the tool, the desired suture tension is established and the energy source is activated (tool and anchor vibrated). Where in intimate contact with the hard tissue wall of the opening the material having thermoplastic properties is liquefied and penetrates into the hard tissue. At the same time the anchor is pushed further into the opening and is finally anchored when the head portion 28 abuts the hard tissue surface. Only at the very end of the anchoring process, shown in FIG. 5, the suture is fixated by liquefaction of the thermoplastic material of the suture anchor. This means that the suture remains slideable (possibly against some friction between suture and tissue inside the hard tissue opening) relative to the anchor during an initial part of the fixation step and therefore the suture tension can still be adapted or maintained up to when the anchor is very close to its final fixated position.

The anchor as illustrated in FIGS. 4 and 5 may include a distal end having a smaller cross section than the rest of the anchor. It may include two eyelets 29 (suture grooves. The suture 22 to be fixated and locked with the aid of the anchor is threaded through the two eyelets 29 and runs along the anchor length e.g. in a suture groove.

The anchor can be fixated in a hard tissue opening 25, wherein the distal anchor end including the two eyelets 29 is made to collapse by the suture being tensioned against the anchor and/or by pushing it against the hard tissue on the bottom of the opening 25 provided for the anchor. The collapse can also be provided by the liquefaction of the thermoplastic material using vibrational energy introduced by tool 31. Such collapse locks the suture 22 because the diameter of the suture eyelet or groove is reduced in such a manner that the suture cannot slide there through anymore.

FIGS. 4 and 5 show, in a very schematic manner, the anchor before and after the fixation of the anchor. In FIG. 4 the anchor is attached to the distal end of the tool 31 is positioned in the mouth of the hard tissue opening 25, the suture 22 runs through the two eyelets 29 and out of the opening 25 at one side of the anchor. Not shown is that the tool is activated by the not shown energy source and the anchor is pushed further into the opening 25. Then the suture 22 can be tensioned or the suture tension be increased. In FIG. 5 fixation of the anchor and locking of the suture 22 are complete. Up to the moment of the collapse of the eyelets 29 *r* the lateral suture groove, the suture 22 may remain slideable relative to the anchor.

Figure 6A:
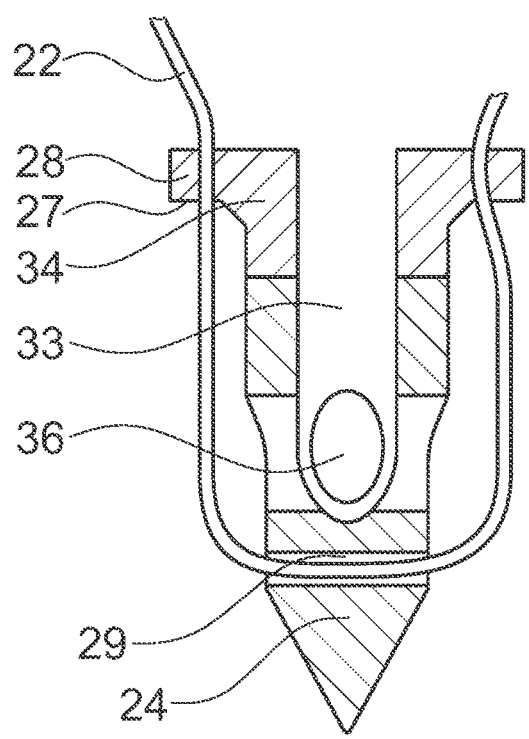
FIG. 6a shows the anchor prior to anchoring, FIG. 6b after anchoring in a bone opening. The anchor includes a sleeve as element to protect the suture from contact with the rim of the bone opening.
Figure 6B:
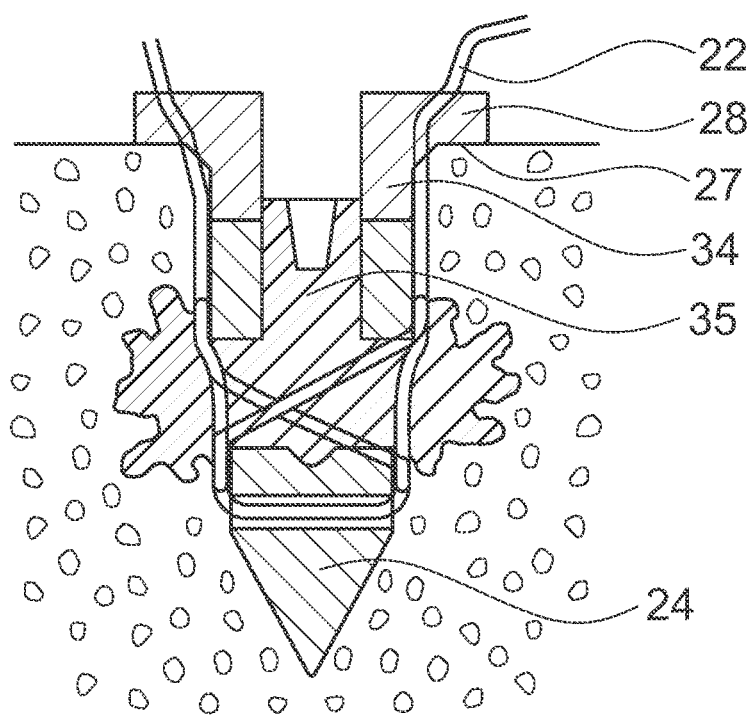
FIG. 6 shows a schematic view of another anchor according to the invention.

FIGS. 6*a* and 6*b* illustrate a further exemplary embodiment of the anchor according to the invention. FIGS. 6*a* and 6*b* show, in a very schematic manner, the anchor before and after the fixation of the anchor. According to this embodiment, the suture anchor 24 includes an inner cavity 33 for insertion of an element made of thermoplastic material. A suture 22 is retained by the anchor, e.g. by being threaded through a distal eyelet 29 or groove. The suture anchor is positioned and/or fixated in a hard tissue opening or is forced into the hard tissue opening with the aid of a pusher tool (not shown) and is held in the hard tissue with the aid of this tool, which may include a distal tool end adapted to fit into the inner cavity 33 or to be cannulated and fit to the sleeve 34, which in this case is able to transfer vibration of the tool to the anchor and the inserted thermoplastic material 35. In an intermediate step, the suture tension is then adjusted or the suture shortened by rotating the suture anchor around its axis with the aid of a tool, while holding the suture 22 such that the suture is wound around the anchor. When the suture tension is satisfactory, the anchor is secured in the hard tissue with the aid of a thermoplastic pin 35 inserted into the inner cavity 33 of the anchor. This inner cavity has at least one opening for releasing the liquefied material or is connected with the circumferential surface of the suture anchor by passages. This opening may be positioned lateral or at the distal end. The winding of the suture around the suture anchor is suitable to adjust the tension of the suture.

The suture anchor includes a sleeve 34. The axial channel of the sleeve has preferably a cross section adapted to the cross section of the inner cavity 33 of the anchor. The sleeve has two channels 27 for the suture. By threading the suture trough these channels and the sleeve friction between the suture and the hard tissue are minimized, also after implantation of the anchor, when the patient is moving again and high forces are affecting the spine and therefore also the suture. The sleeve may include one or two processes overlying the rim of the hard tissue opening. In this case, the suture is lying on the material of the sleeve not directly on the hard tissue.

In an intermediate phase (not shown) the anchor is pushed into a hard tissue opening or, by impaction, into the hard tissue, the suture 22 possibly remaining slideable through the eyelet 29. The suture tension is adjusted by rotation of the anchor, the suture 22 being suitably held such that it is wound around the suture anchor, wherein the latter, for accommodating the wound suture, may include a waist-like area of a reduced cross section. The wound suture is therewith tensioned and at least temporarily locked relative to the anchor and relative to the hard tissue. Thereafter a thermoplastic pin 35 is introduced into the inner cavity 33 of the anchor, as well as the sleeve. For the securing step, the material of the thermoplastic pin 35 is liquefied by a tool introducing mechanical (vibration) energy and pressed through the passages 36 to penetrate the hard tissue surrounding the anchor. FIG. 6b shows the suture anchor after fixation in the hard tissue and after removal of the tool.

The design of the inner cavity 33 of the suture anchor and of the passages 36 relative to the system of channels and/or grooves for retaining the suture are dependent on the individual purpose. The suture anchor may include passages 36 with outer mouths positioned in the anchor area around which the suture 22 is wound. This means that the suture 22 will get into contact with the liquefied material and will be surrounded by it, which, on re-solidification, will not only secure the suture anchor relative to the hard tissue but also the suture relative to the suture anchor. Alternatively, the mouths of the passages 36 may be situated more distally than the anchor area where the suture is situated on the outside of the suture anchor and in particular where it is wound around the suture anchor.

Figure 7:
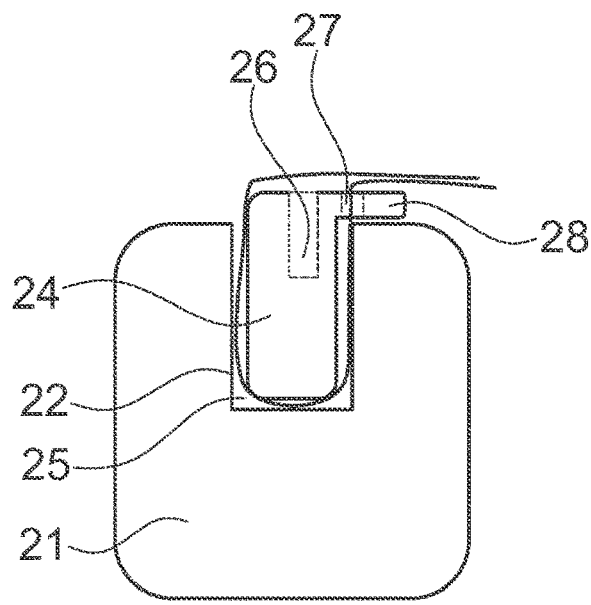
FIG. 7 shows a schematic view of a suture anchor according to the invention. The anchor has at least one element to protect the suture from contact with the rim of the bone opening.
Figure 8:
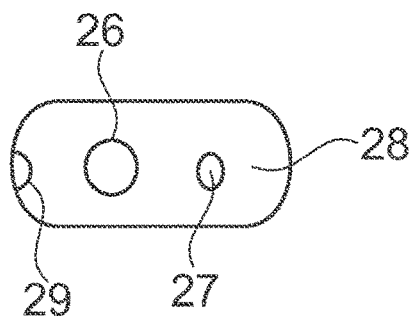
FIG. 8 shows a schematic top view of the suture anchor according to FIG. 7.

FIG. 7 and FIG. 8 show a schematic view of a suture anchor according to the invention. FIG. 7 shows a longitudinal section of the anchor 24 within an opening 25 in a hard tissue 21. FIG. 8 shows a schematic top view of the suture anchor according to FIG. 7. The anchor 24 includes a pin, a head portion 28 in the form of a process and a suture 22. The suture 22 runs laterally around the pin. Therefore, the pin may include a suture groove 29 running across the distal pin face and, in axial direction, along two opposite pin sides. Preferably, the overall cross section of the suture groove is adapted to the suture or sutures to be locked with the aid of the anchor such that the suture(s) running along the groove does not protrude from the groove, i.e. does not get into contact with the hard tissue when the anchor is pushed into the hard tissue opening provided therefore.

The anchor head includes a channel 27 where the suture 22 should be threaded through. The process of the head portion 28 is formed to rest on the outside of the hard tissue 21. This helps to protect the suture 22 that runs over the anchor material but has no contact to the hard tissue surface and especially not to the rim of the opening 25 in the hard tissue. Therefore, friction acting on the suture after implantation (during movement of the spine) can be reduced. Therefore, it is preferred that the rim of the channel 27 is smooth and that also the material of the process is chosen to lower friction (smooth surface). The head portion has a larger cross section than the distal end of the anchor and the opening in the hard tissue such that, when the anchor is introduced into the opening, the proximal face of the head protrudes beyond the proximal end of the opening at least on one side on which the suture groove reaches the head. The channel 27 within the head may be located to extend the suture groove. Alternatively, the head portion can be attached to the pin portion of the anchor such that it is rotatable in order to position the channel to be in line with the suture (groove).

Depending on the method or the location of the anchor according to FIGS. 7 and 8, the head portion includes one or two process having each a suture channel. In case that, after implantation, both ends of the suture should run into the same direction one process is sufficient, wherein on the opposite side the suture groove 29 ends at the proximal face of the anchor (shown in FIG. 8). It is also possible that the suture runs in two different directions (to two adjacent vertebrae, cf. FIG. 9). In this case, the head may include two processes 28 and two channels 27 so that each end of a suture can be positioned on a process.

Figure 9:
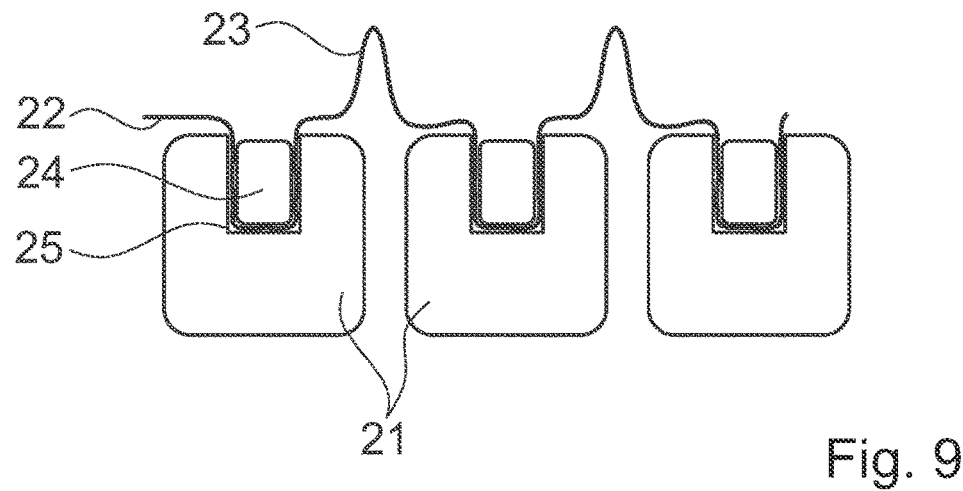
FIG. 9 shows a schematic view of three suture anchors introduced into three adjacent vertebrae before the suture is adjusted or strained.
Figure 10:
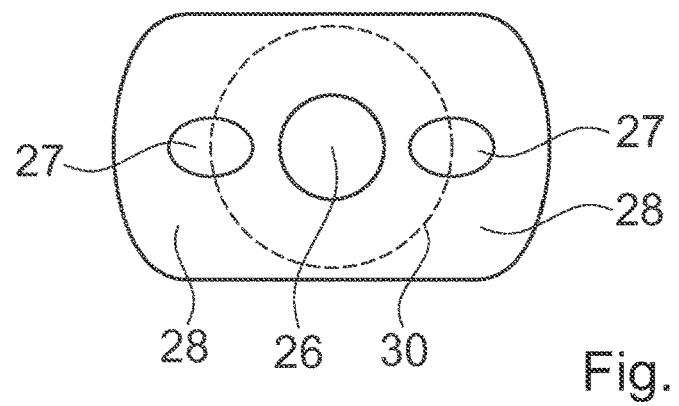
FIG. 10 shows a schematic top view of an anchor having at least one element to protect the suture from contact with the rim of the bone opening.

FIG. 9 illustrates the method according to aspect 2 of the present invention wherein the tension band wiring is used to stabilize more than two neighboring vertebrae 21. In particular in this case, it may be helpful to use suture anchors 24 allowing to tension the suture (knotless) after introduction into the bone opening 25. Consequently, the method for spine stabilization includes a first step wherein at least one suture anchor per lamina arcus vertebrae or per pedicle of at least three adjacent vertebrae is positioned, subsequently the suture is tensioned. Before tensioning of the suture there may be a suture loop 23 between each suture anchor, which allows winding the suture around the anchor for adjusting the suture tension. Thereby it is possible to differ the tension on each side of the vertebrae and adjust the tension to the need of the patient. Subsequently, the anchor is fixed in the bone opening and the suture is fixed (e.g. by liquefaction and re-solidification of a thermoplastic material) relative to the suture anchor. This can be done in parallel (one step) or in subsequent steps, wherein the chronological order can vary and depends on the suture anchor design or the individual demands. Finally, the suture ends of two anchors located at corresponding locations in vertebras being furthest away are knotted together. FIG. 10 shows a schematic top view of a suture anchor according to the invention similar to the one of FIGS. 7 and 8 and being suitable for the method as illustrated in FIG. 9. The head portion includes two processes 28, each having a channel 27 for the suture. Therefore, it is possible that the suture ends of one suture anchor run in two different direction (to two adjacent vertebrae, cf. FIG. 9) after anchoring. Each suture end rests on one process so that friction is reduced. The suture anchor may include a recess 26 or a protrusion 26 to fit to a distal end of a tool used to introduce the anchor, to rotate the anchor and or to introduce mechanical energy into the anchor (such as vibrational energy) for liquefaction of a thermoplastic material. The dotted line 30 indicates the contour of the anchor pin portion. The head portion and the pin portion of the suture anchor may be made as one piece or may be made as two pieces, wherein the head may be configured as a sleeve sitting on the pin portion or may be formed as a plate or disc being attached to the pin portion. This plate or disc may be rotatable in respect to the pin portion of the suture anchor. Therefore, the plate or disc may be introduced into a circumferential furrow or notch of the pin portion.

Figure 11A:
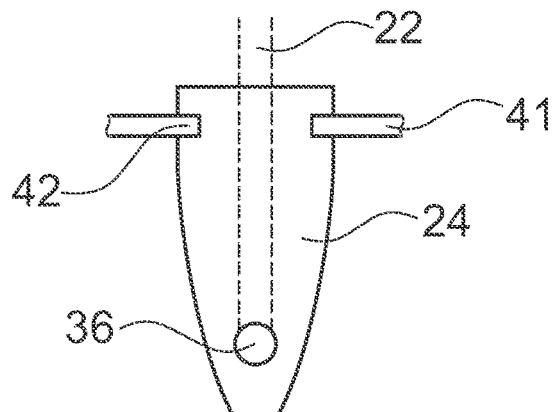
FIG. 11 shows a schematic side view and a top view of an anchor with a plate rotatable with respect to an anchor body that has the pin portion.
Figure 11B:
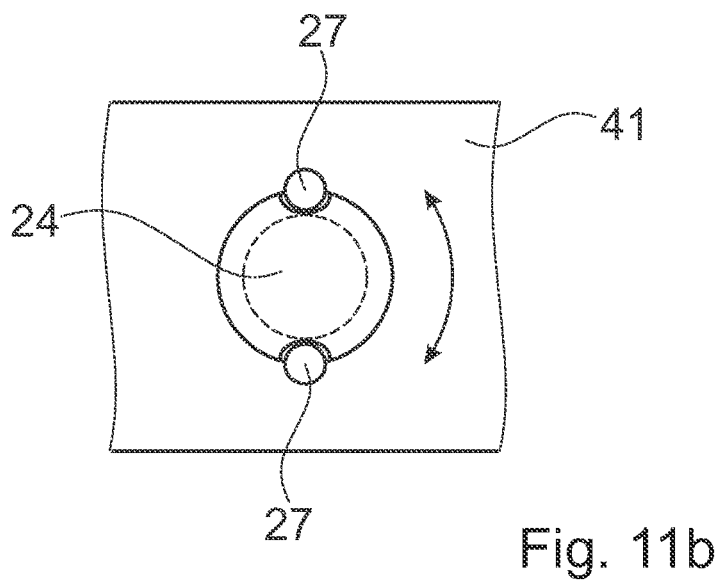

FIGS. 11a and 11b show a suture anchor that has a suture anchor body (forming the pin portion 24) and additionally a disc or plate 41 held relative to the body by being received in a disc retaining groove 42. The disc or plate 41 includes the channels 27 for the suture 22 and is rotatable relative to the body. In this way, the disc or plate 41 protects the suture from contact with the rim of the opening in the bone tissue like in the embodiments of FIGS. 4-6 and nevertheless allows a tensioning of the suture by definition the rotational position of the pin portion—more in general the orientation of the pin portion and the channels 27 can be chosen independently due to the plate or disc 41 being rotatable relative to the pin portion—similarly to the principle illustrated referring to FIG. 6.

The channels may include through openings through the disc or plate or may include notches, for example facing inwardly towards the suture anchor body.

Figure 12:
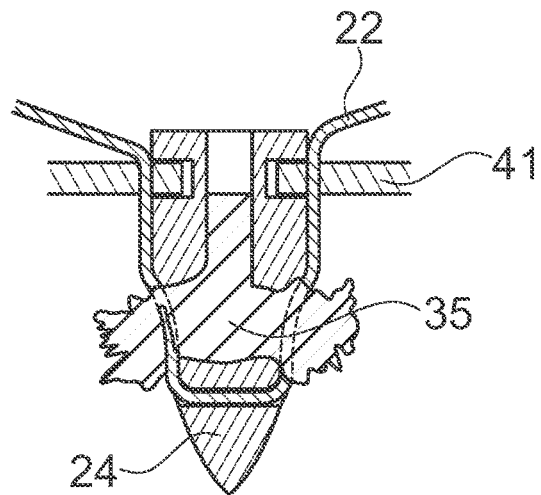
FIG. 12 shows a schematic cross section of an implanted anchor with a disc or plate rotatable with respect to the anchor body.

FIG. 12 shows an embodiment similar to the embodiment of FIG. 6 (and implementing a suture tensioning-by-rotation principle described in detail in WO 2012/100359/EP 2 667 790), but with a plate or disc 41 of the kind described referring to FIG. 11a/11b instead of a sleeve.

What is claimed:

1. A suture anchor for locking a suture relative to a hard tissue, wherein the suture anchor comprises a suture anchor body and is adapted to be fixed within a blind hole in the hard tissue and comprises:
   a material having thermoplastic properties;
   a suture conduit at a distal end of the suture anchor for holding the suture; and
   an element for protecting the suture from contact with a rim of the blind hole in the hard tissue after fixation of the suture anchor by liquefication of the material having thermoplastic properties, said element being disposed at a proximal end of the suture anchor body;
   wherein the element defines a through opening for the suture, said through opening being spaced laterally from the suture anchor body,
   wherein the suture anchor is configured to allow the suture to be fixed relative to the suture anchor in a knot-less manner using the material having thermoplastic properties such that, after fixation, at least one free end of the suture is available for further use outside the hard tissue and the anchor suture;
   wherein the suture anchor is configured such that the suture runs from a proximal end of the through opening over at least a part of the element for protecting the suture from contact with the rim of the blind hole in the hard tissue without contact with the rim of the blind hole in the hard tissue, and wherein the at least one part of the element for protecting the suture from contact with the rim of the blind hole in the hard tissue radially surrounds the proximal end of the through opening.

2. The suture anchor according to claim 1, wherein the suture anchor comprises a collapsible suture guiding conduit that is formed from the material having thermoplastic properties.

3. The suture anchor according to claim 1, wherein the suture anchor body defines the suture conduit, and wherein the element for protecting the suture from contact with the rim of the blind hole in the hard tissue comprises a sleeve shaped to traverse the rim of the blind hole in the hard tissue and defines the through opening for the suture, said element fitting to the proximal end of the suture anchor body.

4. The suture anchor according to claim 3, wherein the sleeve is rotatable relative to the suture anchor body.

5. The suture anchor according to claim 1, wherein the suture anchor body includes the suture conduit, and wherein the element for protecting the suture from contact with the rim of the blind hole in the hard tissue and comprises a plate or disc shaped to be arranged proximally of the rim of the blind hole in the hard tissue and the plate or disc comprises the through opening for the suture, the plate or disc being designed to fit to the proximal end of the suture anchor body.

6. The suture anchor according to claim 5, wherein the plate or disc is rotatable relative to the anchor body.

7. The suture anchor according to claim 1, wherein the element for protecting the suture from contact with the rim of the blind hole in the hard tissue comprises a proximal lateral projection of the suture anchor, the proximal lateral projection comprising the through opening for the suture and being shaped to shield the suture from the rim of the blind hole in the hard tissue.

8. The suture anchor according to claim 1, wherein the element for protecting the suture from contact with the rim of the blind hole in the hard tissue has an extension causing a minimal distance between the suture and the hard tissue and the rim of the blind hole in the hard tissue of 2 mm.

9. The suture anchor according to claim 1, wherein the element for protecting the suture from contact with the rim of the blind hole in the hard tissue is formed from a flexible foil material.

10. The suture anchor according to claim 1, wherein the element for protecting the suture from contact with the rim of the blind hole in the hard tissue is formed from a thermoplastic foil material.

11. The suture anchor according to claim 1, wherein for the element for protecting the suture from contact with the rim of the blind hole in the hard tissue at least one of the following conditions holds: the element has a thickness of at most 1<mm and a Young's modulus of at most 0.5 GPa; the element has a thickness of at most 0.5 mm.

12. The suture anchor according to claim 1, wherein the element for protecting the suture from contact with the rim of the blind hole in the hard tissue, with the exception of the through opening, is rotationally symmetrical around a suture anchor axis.

13. The suture anchor according to claim 1, wherein the suture anchor is configured such that, after introduction of the suture anchor within the blind hole in the hard tissue, the element for protecting the suture from contact with the rim of the blind hole in the hard tissue covers the rim of the blind hole in the hard tissue.

* * * * *